United States Patent
Wan et al.

(10) Patent No.: US 11,220,533 B2
(45) Date of Patent: Jan. 11, 2022

(54) HUMAN SDR5-FC RECOMBINANT FUSION PROTEIN AND APPLICATION THEREOF

(71) Applicant: SHENZHEN ZHONGKE AMSHENN PHARMACEUTICAL CO., LTD., Shenzhen (CN)

(72) Inventors: Xiaochun Wan, Shenzhen (CN); Junxin Li, Shenzhen (CN); Qian Chen, Shenzhen (CN); Qingmei Zhang, Shenzhen (CN)

(73) Assignee: SHENZHEN ZHONGKE AMSHENN PHARMACEUTICAL CO., LTD., Shenzhen (CN)

( * ) Notice: Subject to any disclaimer, the term of this patent is extended or adjusted under 35 U.S.C. 154(b) by 521 days.

(21) Appl. No.: 16/344,365

(22) PCT Filed: Jul. 11, 2016

(86) PCT No.: PCT/CN2016/089650
§ 371 (c)(1),
(2) Date: Apr. 24, 2019

(87) PCT Pub. No.: WO2017/128630
PCT Pub. Date: Aug. 3, 2017

(65) Prior Publication Data
US 2019/0352354 A1 Nov. 21, 2019

(30) Foreign Application Priority Data

Jan. 29, 2016 (CN) .......................... 201610067931.2
Mar. 18, 2016 (CN) .......................... 201610161270.X

(51) Int. Cl.
| | | |
|---|---|---|
| A61K 38/17 | (2006.01) | |
| A61K 38/19 | (2006.01) | |
| A61K 38/00 | (2006.01) | |
| A61P 1/16 | (2006.01) | |
| A61P 37/02 | (2006.01) | |
| C07K 14/47 | (2006.01) | |
| C12N 15/62 | (2006.01) | |

(52) U.S. Cl.
CPC .......... *C07K 14/4702* (2013.01); *C12N 15/62* (2013.01); *A61K 38/00* (2013.01)

(58) Field of Classification Search
CPC .... A61K 31/7088; A61K 38/00; A61K 38/17; A61K 38/19; A61P 1/16; A61P 37/02; C07K 14/4702; C07K 14/70578; C07K 2319/30; C07K 14/47
See application file for complete search history.

(56) References Cited

U.S. PATENT DOCUMENTS

| | | | |
|---|---|---|---|
| 6,313,269 | B1 | 11/2001 | Deen et al. |
| 10,918,739 | B2 * | 2/2021 | Ma ................... A61K 39/3955 |
| 2018/0161450 | A1 * | 6/2018 | Ma ................... A61K 39/3955 |

FOREIGN PATENT DOCUMENTS

| | | |
|---|---|---|
| CN | 102949708 A | 3/2013 |
| CN | 104710533 A | 6/2015 |
| CN | 105061604 A | 11/2015 |
| CN | 105693867 A | 6/2016 |

OTHER PUBLICATIONS

Acute Hepatitis B from Merck Manual, pp. 1-5. Accessed Apr. 19, 2021. (Year: 2021).*
Chronic Hepatitis B from Merck Manual, pp. 1-5. Accessed Apr. 19, 2021. (Year: 2021).*
Liver Injury Caused by Drugs from Merck Manual, pp. 1-6. Accessed Apr. 19, 2021. (Year: 2021).*
Badmann A, Langsch S, Keogh A, Brunner T, Kaufmann T, Corazza N., TRAIL enhances paracetamol-induced liver sinusoidal endothelial cell death in a Bim- and Bid-dependent manner. Cell Death and Disease. Dec. 20, 2012; 3:e447;doi:10.1038/cddis. 2012.185, pp. 1-11, Macmillan Publisher Limited, published online www.nature.com/cddis.
Badmann A, Keough A, Kaufmann T, Bouillet P, Brunner T, Corazza N. Role of TRAIL and the pro-apoptotic Bcl-2 homolog Bim in acetaminophen-induced liver damage. Cell Death and Disease. Jun. 9, 2011; 2:e171;doi:10.1038/cddis. 2011.55, pp. 1-7, Macmillan Publisher Limited, published online www.nature.com/cddis.
Yin Xiao-Ming, Ding Wen-Xing, Death receptor activation-induced hepatocyte apoptosis and liver injury. Current Molecular Medicine, Sep. 30, 2003; pp. 491-508, vol. 3, No. 6, Bentham Science Publishers Ltd.
Hajime Higuchi, Gregory J. Gores, Mechanisms of Liver Injury: An Overview. Current Molecular Medicine, Sep. 30, 2003; pp. 483-490, vol. 3, No. 6, Bentham Science Publishers Ltd.

* cited by examiner

*Primary Examiner* — Julie Ha
(74) *Attorney, Agent, or Firm* — Bayramoglu Law Offices LLC

(57) ABSTRACT

An sDR5-Fc recombinant fusion protein having amino acid sequence of SEQ ID NO: 2 and a gene encoding the protein and having a nucleotide sequence as shown in SEQ ID NO: 1 are provided. Further, applications of the protein and the gene in the preparation of medicament for preventing and treating autoimmune hepatitis or drug-induced liver injury are provided.

16 Claims, 19 Drawing Sheets

Specification includes a Sequence Listing.

SEQUENCE LISTING

```
<160> NUMBER OF SEQ ID NOS: 7

<210> SEQ ID NO 1
<211> LENGTH: 1101
<212> TYPE: DNA
<213> ORGANISM: Artificial Sequence
<220> FEATURE:
<223> OTHER INFORMATION: A synthetized DNA sequence of ZJ501-5

<400> SEQUENCE: 1
atgggtgtac tgctcacaca gaggacgctg ctcagtctgg tccttgcact cctgtttcca      60
agcatggcga gcatgtccag cccctcagag ggattgtgtc cacctggaca ccatatctca     120
gaagacggta gagattgcat ctcctgcaaa tatggacagg actatagcac tcactggaat     180
gacctccttt tctgcttgcg ctgcaccagg tgtgattcag gtgaagtgga gctaagtccc     240
tgcaccacga ccagaaacac agtgtgtcag tgcgaagaag gcaccttccg ggaagaagat     300
tctcctgaga tgtgccggaa gtgccgcaca gggtgtccca gagggatggt caaggtcggt     360
gattgtacac cctggagtga catcgaatgt gtccacaaag aagagcccaa atcttgtgac     420
aaaactcaca catgcccacc gtgcccagca cctgaactcc tggggggacc gtcagtcttc     480
ctcttccccc caaaacccaa ggacaccctc atgatctccc ggacccctga ggtcacatgc     540
gtggtggtgg acgtgagcca cgaagaccct gaggtcaagt tcaactggta cgtggacggc     600
gtggaggtgc ataatgccaa gacaaagccg cgggaggagc agtacaacag cacgtaccgt     660
gtggtcagcg tcctcaccgt cctgcaccag gactggctga atggcaagga gtacaagtgc     720
aaggtctcca acaaagccct cccagccccc atcgagaaaa ccatctccaa agccaaaggg     780
cagccccgag aaccacaggt gtacaccctg cccccatccc gggatgagct gaccaagaac     840
caggtcagcc tgacctgcct ggtcaaaggc ttctatccca gcgacatcgc cgtggagtgg     900
gagagcaatg ggcagccgga gaacaactac aagaccacgc ctcccgtgct ggactccgac     960
ggctccttct tcctctacag caagctcacc gtggacaaga gcaggtggca gcaggggaac    1020
gtcttctcat gctccgtgat gcatgaggct ctgcacaacc actacacgca gaagagcctc    1080
tccctgtctc cgggtaaatg a                                              1101

<210> SEQ ID NO 2
<211> LENGTH: 366
<212> TYPE: PRT
<213> ORGANISM: Artificial Sequence
<220> FEATURE:
<223> OTHER INFORMATION: A modified amino acid sequence of ZJ501-5

<400> SEQUENCE: 2

Met Gly Val Leu Leu Thr Gln Arg Thr Leu Leu Ser Leu Val Leu Ala
 1               5                  10                  15

Leu Leu Phe Pro Ser Met Ala Ser Met Ser Ser Pro Ser Glu Gly Leu
                20                  25                  30
```

-continued

```
Cys Pro Pro Gly His His Ile Ser Glu Asp Gly Arg Asp Cys Ile Ser
        35                  40                  45

Cys Lys Tyr Gly Gln Asp Tyr Ser Thr His Trp Asn Asp Leu Leu Phe
    50                  55                  60

Cys Leu Arg Cys Thr Arg Cys Asp Ser Gly Glu Val Glu Leu Ser Pro
65                  70                  75                  80

Cys Thr Thr Thr Arg Asn Thr Val Cys Gln Cys Glu Glu Gly Thr Phe
                85                  90                  95

Arg Glu Glu Asp Ser Pro Glu Met Cys Arg Lys Cys Arg Thr Gly Cys
            100                 105                 110

Pro Arg Gly Met Val Lys Val Gly Asp Cys Thr Pro Trp Ser Asp Ile
        115                 120                 125

Glu Cys Val His Lys Glu Glu Pro Lys Ser Cys Asp Lys Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Asp Glu Leu Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365

<210> SEQ ID NO 3
<211> LENGTH: 425
<212> TYPE: PRT
<213> ORGANISM: Artificial Sequence
<220> FEATURE:
<223> OTHER INFORMATION: A modified amino acid sequence of ZJ501-1

<400> SEQUENCE: 3

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30
```

Arg Val Pro Lys Thr Leu Val Val Ala Ala Val Leu Leu Leu
            35                  40                  45

Val Ser Ala Glu Ser Ala Leu Ile Thr Gln Gln Asp Leu Ala Pro Gln
 50                  55                  60

Gln Arg Ala Ala Pro Gln Gln Lys Arg Ser Ser Pro Ser Glu Gly Leu
 65                  70                  75                  80

Cys Pro Pro Gly His His Ile Ser Glu Asp Gly Arg Asp Cys Ile Ser
                 85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
            115                 120                 125

Cys Thr Thr Thr Arg Asn Thr Val Cys Gln Cys Glu Glu Gly Thr Phe
130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Gly Ser Ser Asn Thr Lys Val Asp Lys Lys
            180                 185                 190

Val Glu Pro Lys Ser Cys Asp Lys Thr His Thr Cys Pro Pro Cys Pro
            195                 200                 205

Ala Pro Glu Leu Leu Gly Gly Pro Ser Val Phe Leu Phe Pro Pro Lys
            210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                245                 250                 255

Val Asp Gly Val Glu Val His Asn Ala Lys Thr Lys Pro Arg Glu Glu
            260                 265                 270

Gln Tyr Asn Ser Thr Tyr Arg Val Val Ser Val Leu Thr Val Leu His
            275                 280                 285

Gln Asp Trp Leu Asn Gly Lys Glu Tyr Lys Cys Lys Val Ser Asn Lys
290                 295                 300

Ala Leu Pro Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Asp Glu Leu
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
            355                 360                 365

Tyr Lys Thr Thr Pro Pro Val Leu Asp Ser Asp Gly Ser Phe Phe Leu
370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Pro Gly Lys
            420                 425

<210> SEQ ID NO 4
<211> LENGTH: 414
<212> TYPE: PRT

<213> ORGANISM: Artificial Sequence
<220> FEATURE:
<223> OTHER INFORMATION: A modified amino acid sequence of ZJ501-2

<400> SEQUENCE: 4

Met Glu Gln Arg Gly Gln Asn Ala Pro Ala Ala Ser Gly Ala Arg Lys
1 5 10 15

Arg His Gly Pro Gly Pro Arg Glu Ala Arg Gly Ala Arg Pro Gly Pro
20 25 30

Arg Val Pro Lys Thr Leu Val Leu Val Val Ala Ala Val Leu Leu Leu
35 40 45

Val Ser Ala Glu Ser Ala Leu Ile Thr Gln Gln Asp Leu Ala Pro Gln
50 55 60

Gln Arg Ala Ala Pro Gln Gln Lys Arg Ser Ser Pro Ser Glu Gly Leu
65 70 75 80

Cys Pro Pro Gly His His Ile Ser Glu Asp Gly Arg Asp Cys Ile Ser
85 90 95

Cys Lys Tyr Gly Gln Asp Tyr Ser Thr His Trp Asn Asp Leu Leu Phe
100 105 110

Cys Leu Arg Cys Thr Arg Cys Asp Ser Gly Glu Val Glu Leu Ser Pro
115 120 125

Cys Thr Thr Thr Arg Asn Thr Val Cys Gln Cys Glu Glu Gly Thr Phe
130 135 140

Arg Glu Glu Asp Ser Pro Glu Met Cys Arg Lys Cys Arg Thr Gly Cys
145 150 155 160

Pro Arg Gly Met Val Lys Val Gly Asp Cys Thr Pro Trp Ser Asp Ile
165 170 175

Glu Cys Val His Lys Glu Glu Pro Lys Ser Cys Asp Lys Thr His Thr
180 185 190

Cys Pro Pro Cys Pro Ala Pro Glu Leu Leu Gly Gly Pro Ser Val Phe
195 200 205

Leu Phe Pro Pro Lys Pro Lys Asp Thr Leu Met Ile Ser Arg Thr Pro
210 215 220

Glu Val Thr Cys Val Val Val Asp Val Ser His Glu Asp Pro Glu Val
225 230 235 240

Lys Phe Asn Trp Tyr Val Asp Gly Val Glu Val His Asn Ala Lys Thr
245 250 255

Lys Pro Arg Glu Glu Gln Tyr Asn Ser Thr Tyr Arg Val Val Ser Val
260 265 270

Leu Thr Val Leu His Gln Asp Trp Leu Asn Gly Lys Glu Tyr Lys Cys
275 280 285

Lys Val Ser Asn Lys Ala Leu Pro Ala Pro Ile Glu Lys Thr Ile Ser
290 295 300

Lys Ala Lys Gly Gln Pro Arg Glu Pro Gln Val Tyr Thr Leu Pro Pro
305 310 315 320

Ser Arg Asp Glu Leu Thr Lys Asn Gln Val Ser Leu Thr Cys Leu Val
325 330 335

Lys Gly Phe Tyr Pro Ser Asp Ile Ala Val Glu Trp Glu Ser Asn Gly
340 345 350

Gln Pro Glu Asn Asn Tyr Lys Thr Thr Pro Pro Val Leu Asp Ser Asp
355 360 365

Gly Ser Phe Phe Leu Tyr Ser Lys Leu Thr Val Asp Lys Ser Arg Trp
370 375 380

Gln Gln Gly Asn Val Phe Ser Cys Ser Val Met His Glu Ala Leu His

Asn His Tyr Thr Gln Lys Ser Leu Ser Leu Ser Pro Gly Lys
                    405                 410

<210> SEQ ID NO 5
<211> LENGTH: 384
<212> TYPE: PRT
<213> ORGANISM: Artificial Sequence
<220> FEATURE:
<223> OTHER INFORMATION: A modified amino acid sequence of ZJ501-3

<400> SEQUENCE: 5

Met Gly Val Leu Leu Thr Gln Arg Thr Leu Leu Ser Leu Val Leu Ala
1               5                   10                  15

Leu Leu Phe Pro Ser Met Ala Ser Met Ile Thr Gln Gln Asp Leu Ala
            20                  25                  30

Pro Gln Gln Arg Ala Ala Pro Gln Gln Lys Arg Ser Ser Pro Ser Glu
        35                  40                  45

Gly Leu Cys Pro Pro Gly His His Ile Ser Glu Asp Gly Arg Asp Cys
    50                  55                  60

Ile Ser Cys Lys Tyr Gly Gln Asp Tyr Ser Thr His Trp Asn Asp Leu
65                  70                  75                  80

Leu Phe Cys Leu Arg Cys Thr Arg Cys Asp Ser Gly Glu Val Glu Leu
                85                  90                  95

Ser Pro Cys Thr Thr Thr Arg Asn Thr Val Cys Gln Cys Glu Glu Gly
            100                 105                 110

Thr Phe Arg Glu Glu Asp Ser Pro Glu Met Cys Arg Lys Cys Arg Thr
        115                 120                 125

Gly Cys Pro Arg Gly Met Val Lys Val Gly Asp Cys Thr Pro Trp Ser
    130                 135                 140

Asp Ile Glu Cys Val His Lys Glu Glu Pro Lys Ser Cys Asp Lys Thr
145                 150                 155                 160

His Thr Cys Pro Pro Cys Pro Ala Pro Glu Leu Leu Gly Gly Pro Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
        195                 200                 205

Glu Val Lys Phe Asn Trp Tyr Val Asp Gly Val Glu Val His Asn Ala
    210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
        275                 280                 285

Pro Pro Ser Arg Asp Glu Leu Thr Lys Asn Gln Val Ser Leu Thr Cys
    290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser

```
                340             345             350
Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
    370                 375                 380

<210> SEQ ID NO 6
<211> LENGTH: 373
<212> TYPE: PRT
<213> ORGANISM: Artificial Sequence
<220> FEATURE:
<223> OTHER INFORMATION: A modified amino acid sequence of ZJ501-4

<400> SEQUENCE: 6

Met Gly Val Leu Leu Thr Gln Arg Thr Leu Leu Ser Leu Val Leu Ala
1               5                   10                  15

Leu Leu Phe Pro Ser Met Ala Ser Met Ala Ala Pro Gln Gln Lys Arg
            20                  25                  30

Ser Ser Pro Ser Glu Gly Leu Cys Pro Pro Gly His His Ile Ser Glu
        35                  40                  45

Asp Gly Arg Asp Cys Ile Ser Cys Lys Tyr Gly Gln Asp Tyr Ser Thr
    50                  55                  60

His Trp Asn Asp Leu Leu Phe Cys Leu Arg Cys Thr Arg Cys Asp Ser
65                  70                  75                  80

Gly Glu Val Glu Leu Ser Pro Cys Thr Thr Arg Asn Thr Val Cys
                85                  90                  95

Gln Cys Glu Glu Gly Thr Phe Arg Glu Glu Asp Ser Pro Glu Met Cys
            100                 105                 110

Arg Lys Cys Arg Thr Gly Cys Pro Arg Gly Met Val Lys Val Gly Asp
        115                 120                 125

Cys Thr Pro Trp Ser Asp Ile Glu Cys Val His Lys Glu Glu Pro Lys
    130                 135                 140

Ser Cys Asp Lys Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
    210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Asp Glu Leu Thr Lys Asn Gln
        275                 280                 285

Val Ser Leu Thr Cys Leu Val Lys Gly Phe Tyr Pro Ser Asp Ile Ala
    290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
```

-continued

```
                325                 330                 335
Thr Val Asp Lys Ser Arg Trp Gln Gln Gly Asn Val Phe Ser Cys Ser
            340                 345                 350

Val Met His Glu Ala Leu His Asn His Tyr Thr Gln Lys Ser Leu Ser
        355                 360                 365

Leu Ser Pro Gly Lys
    370

<210> SEQ ID NO 7
<211> LENGTH: 11
<212> TYPE: PRT
<213> ORGANISM: Artificial Sequence
<220> FEATURE:
<223> OTHER INFORMATION: N-terminal sequence to be cut

<400> SEQUENCE: 7

Ile Thr Gln Gln Asp Leu Ala Pro Gln Gln Arg
1               5                   10
```

HUMAN SDR5-FC RECOMBINANT FUSION PROTEIN AND APPLICATION THEREOF

CROSS REFERENCE TO THE RELATED APPLICATIONS

This application is the national phase entry of International Application No. PCT/CN2016/089650, filed on Jul. 11, 2016, which is based upon and claims priority to Chinese Patent Application No. 201610067931.2, filed on Jan. 29, 2016, and Chinese Patent Application No. 201610161270.X, filed on Mar. 18, 2016, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBBJCH007-PKG_SL.txt, created on 05/25/2021 and is 19,604 bytes in size.

TECHNICAL FIELD

The present invention relates to the field of recombinant proteins and medicine, and in particular to a novel human sDR5-Fc recombinant fusion protein and an application thereof.

BACKGROUND

According to World Health Organization, the proportion of hepatitis patients to healthy people in the world is about $\frac{1}{12}$ at the present stage, that is, there may be one hepatitis patient among every twelve people, and this proportion is nearly ten times that of HIV (human immunodeficiency virus) infected people. Currently, there are nearly 500 million patients which have hepatitis such as hepatitis B, hepatitis C, etc. in various countries around the world, accounting for $\frac{1}{12}$ of the global population. China is the country with the highest number of hepatitis patients, and every year, nearly 300,000 people die of liver-related diseases such as liver cirrhosis and liver cancer. More than 500,000 people worldwide die of primary liver cancer each year, specifically, up to 80 percent of the primary liver cancer is caused by hepatitis. Among the 400 million hepatitis patients, 75 percent of them live in Asia, and China is the country with the heaviest burden of hepatitis and liver cancer patients in the world. The annual cost for hepatitis B treatment in China is more than 100 billion yuan.

Drug-induced liver injury (DILI) refers to liver injury induced by various prescription or over-the-counter chemical drugs, biological agents, traditional Chinese medicines, natural medicines, health care products, dietary supplements, metabolites and excipients thereof, etc. Patients with or without a liver underlying disease may have drug-induced liver injury after using the drug. DILI is one of the most common and serious adverse drug reactions, and severe cases may cause acute liver failure (ALF) or even death. Drug-induced liver injury is the most common reason for stopping the developments of new drugs and withdrawing new drugs from the market. In China, due to the continuous increase of drugs, the promotion of new drugs, and the development and clinical applications of the various health care drugs in recent years, the incidence of DILI has increased significantly as well.

It is known that more than 1,100 approved drugs worldwide have potential hepatotoxicity, including nonsteroidal anti-inflammatory drugs (NSAIDs), anti-infective drugs (including anti-tuberculosis drugs), anti-tumor drugs, central nervous system drugs, cardiovascular system drugs, metabolic disease drugs, hormonal drugs, certain biological preparations, etc. Among the Europeans and Americans, the three most common types of drugs that may cause DILI are NSAIDs, antibiotics, and central nervous system drugs (e.g., the tacrine for treatment of senile dementia), and the acetaminophen (APAP) is the most common drug that may cause DILI. Another study reported that the top three drugs that cause DILI were: APAP, highly active antiretroviral drugs, and anti-tuberculosis drugs (e.g., isoniazid, rifampicin). Moreover, APAP is the leading cause of acute liver failure. The mortality rate caused by APAP is 500 cases/year in the UK. According to the U.S. Center for Disease Control (CDC), 1600 cases of acute liver failure occur each year in the United States, and 41% of DILI are caused by APAP. In Asia, the causes of the drug-induced liver injury are different from those in Europe and the United States. China is a high risk area for tuberculosis. In recent years, liver injury caused by anti-tuberculosis drugs has ranked first in the drug-induced liver injury in China.

Drug-induced liver injury patients are mainly treated with drugs that protect the liver, reduce enzymes, eliminate jaundice and promote growth of liver cells, and the patients with high serum bilirubin are supplemented with artificial liver treatment. The mild patients may recover quickly after stopping the drugs or after symptomatic treatment such as general liver protection, etc., the severe patients need hospitalization, and very few die due to liver failure. The basic treatment principles of DILI are: (1) timely stopping the use of suspicious liver injury drugs, trying to avoid re-use of the suspicious drugs or other drugs of the same class; (2) selecting appropriate medical treatment according to the clinical type of DILI; (3) considering liver transplantation for the hepatic encephalopathy and acute hepatic failure/subacute liver failure with severe coagulopathy, and decompensated cirrhosis.

To date, DILI still lacks special treatments. The treatment drugs mainly include the following types:

(1) N-acetylcysteine (NAC): NAC is used to treat DILI caused by APAP. For children, since the result of using NAC to treat ALF that is not caused by APAP does not coincide with that from a randomized controlled treatment study, NAC is not recommended for the treatment of drug-induced ALF that is not caused by APAP, especially for children aged from 0 to 2 years old. However, it is known that more than 1,100 drugs worldwide can cause DILI, and APAP is only one of them. Different kinds of drugs have different mechanisms for causing liver injury, so the therapeutic range of NAC drugs is very limited. Moreover, NAC has certain side effects: 1) it has a stimulating effect on the respiratory mucosa, sometimes causing cough or bronchospasm; and 2) the NAC aqueous solution has the smell of hydrogen sulfide, causing nausea, vomiting, nasal discharge, gastritis, etc. in some patients. Therefore, the rate of administration of NAC needs to be strictly controlled during the treatment of DILI to avoid adverse reactions.

(2) Glucocorticoids: glucocorticoids are applicable for the treatment of immune-mediated DILI. AIH-like DILI with autoimmune features responds well to glucocorticoid therapy and are less likely to relapse after discontinuation of the glucocorticoids.

(3) Magnesium isoglycyrrhizinate: China Food and Drug Administration (CFDA) has approved magnesium isoglycyrrhizinate for the treatment of acute hepatocellular DILI or mixed DILI with significantly elevated alanine transaminase (ALT), thereby reducing ALT level of DILI patients.

However, the exact efficacy of the above drugs needs to be confirmed by a rigorous prospective randomized controlled study. Moreover, these drugs usually have narrow therapeutic ranges and have certain effects on the mild patients, but the effects of these drugs on the severe patients are limited, or two drugs used in conjunction may even cause deterioration of the illness. Furthermore, the drugs have unclear effect target and certain side effects, so drug-induced liver injury still lacks specific and safe treatment measures. Therefore, the species and efficacies of the existing drugs for treating DILI are limited, and it is urgent to develop new therapeutic drugs.

Autoimmune hepatitis refers to an inflammatory liver disease mediated by an autoimmune response, clinical features thereof are elevated serum transaminases in varying degrees, hypergammaglobulinemia and positive autoantibodies, and histological features thereof are interface hepatitis infiltrated with lymphocyte and plasmacyte. The severe cases of the autoimmune hepatitis may rapidly progress to liver cirrhosis and liver failure. In the United States, patients with autoimmune hepatitis account for 10%-15% of patients with chronic liver disease. In China, the tendency of autoimmune hepatitis is increasing year by year, many patients have poor response to immunosuppressive therapy, and end-stage patients require liver transplantation. However, the recurrence rate in the first year after liver transplantation is 7%-10%, and the recurrence rate in 5 years after liver transplantation is 65%-70%. Therefore, it is necessary to develop safer and more effective therapeutic drugs. Con A, a plant-derived lectin-like polysaccharide, is a T cell activator. In 1992, Tiegs et al reported that intravenous injection of Con A may induce liver tissue necrosis in large areas, cause extensive lymphocytic infiltration, increase hepatocyte apoptosis, and cause elevated serum ALT and AST. Treatment with immunosuppressive agents such as cyclosporine A, FK506, dexamethasone, etc. before injection of Con A can completely avoid or reduce the occurrence of liver injury, indicating that Con A-induced liver injury in mice is closely related to liver immune response, which has many similarities, in terms of the pathogenic characteristics thereof, with human autoimmune liver disease or viral hepatitis that we currently know in the pathological mechanisms. The Con A-induced acute liver injury model has the advantages of short modeling period, high reproducibility, and being similar to human hepatitis in the pathogenesis, etc., which has been widely used in the research on hepatitis treatment methods and mechanisms.

The occurrence and development between autoimmune hepatitis and drug-induced hepatitis have different symptoms, but have common characteristics. Ultimately, the key steps thereof both involve rapid apoptosis of hepatocytes. Apoptosis is the active cell death process caused by the activation of intracellular apoptosis mechanisms after cells receive extracellular death signals, which is essential for maintaining the stability of internal environment of the human body and has an important biological role. However, when liver hepatitis occurs, multiple stressors such as cytokines, oxidative stress, DNA damage, etc. activate apoptotic signals of cells, causing massive hepatocyte death. Apoptosis is the main manner of cell death caused by hepatitis, and is considered to be the basic mechanism of occurrence and development of diseases, and the related molecules thereof have become key targets for the treatment of the liver hepatitis as well. Inhibition of apoptosis can effectively prevent the development of the liver hepatitis.

Death receptor 5 (DR5), a member of the tumor necrosis factor (TNF) receptor family, is a specific, high-affinity receptor for TNF-related apoptosis-inducing ligand (TRAIL), which has low expression on the surface of normal cells and high expression in tissues of inflammation, ischemia or cancer. The full-length human DR5 contains 411 amino acids and is a type I transmembrane glycoprotein, the N-terminus thereof is located at extracellular spaces, and the C-terminus is located at intracellular spaces, with single transmembrane. Specifically, amino acids at sites 1 to 55 belong to signal peptides, and the amino acids at sites 84 to 179 are a chain-like binding domain containing two cysteine-rich repeating functional domains, the amino acids at sites 184 to 206 belong to a transmembrane domain, and the intracellular domain contains a death domain. Intracellular signaling pathways can be effectively activated when DR5 combines with TRAIL, inducing apoptosis.

Drugs and metabolites thereof can activate a variety of death signaling pathways, including hepatocyte mitochondrial damage, oxidative stress, death ligands, and high receptor expression, etc., thereby promoting apoptosis. APAP can induce the production of pro-apoptotic Bcl-2 protein homolog Bim and death ligand TRAIL, which leads to the occurrence of liver injury (Badmann A, Langsch S, Keogh A, Bmnner T, Kaufmann T, Corazza N. TRAIL enhances paracetamol-induced liver sinusoidal endothelial cell death in a Bim- and Bid-dependent manner. Cell Death Dis. 2012 Dec. 20; 3:e447. Badmann A, Keough A, Kaufmann T, Bouillet P, Brunner T, Corazza N. Role of TRAIL and the pro-apoptotic Bcl-2 homolog Bim in acetaminophen-induced liver damage. Cell Death Dis. 2011 Jun. 9; 2:e171.). Anti-tuberculosis drugs can cause immune liver injury, and hepatocytes can be directly damaged by oxidative stress products produced in inflammatory reactions, or apoptosis can be induced by death receptor signaling pathways. Hepatocyte death and intrahepatic and extrahepatic obstruction cause abnormal bile acid metabolism, and the elevated bile acid level, which upregulates expression of DR5, and induces the increase of hepatocyte apoptosis through TRAIL. When the liver suffers from "ischemia and hypoxia", it was found that in the process of hypoxia/recovery of oxygen in human hepatocytes, the expression of DR5 is upregulated, resulting in increased TRAIL-induced apoptosis. Therefore, the TRAIL-DR5-induced apoptosis system is involved in multiple stages of the occurrence and development of liver injury, which is one of the key factors for rapid apoptosis of hepatocytes in large quantities. Targeting the TRAIL-DR5 system, inhibition of apoptosis can effectively prevent the occurrence and development of liver injury.

Soluble DR5 (sDR5) is a soluble form of DR5 that does not contain a transmembrane domain, which is secreted outside the cell because the transmembrane domain lacks and sDR5 cannot be expressed on the cell membrane. Although sDR5 retains the activity capable of being in combination with TRAIL ligands, it is unable to transmit apoptotic signals to cells, blocking the apoptosis mediated by TRAIL-DR5. Moreover, sDR5 is a protein in human body, which has the advantages of low toxicity and no immunogenicity, and has great potential as an important therapeutic drug for diseases including liver hepatitis and liver injury.

At present, the sDR5-Fc protein as a drug has not been approved at home and abroad, and belongs to the national first class new drugs. No company in the world can produce sDR5-Fc protein on a large scale in a Good Manufacturing Practice (GMP). Only six companies, i.e., Sigma (Art. No. D9563, discontinued), Enzo life sciences (Art. No. ALX-522-005), EXBIO antibodies (Art. No. EXB0007), Abcam (Art. No. AB83547), R&D systems (Art. No. 631-T2) and Sino Biological (Art. No. 10465-H03H), produce sDR5-Fc protein as a biochemical reagent. The DR5 gene sequences used in these six products are not identical, the types of engineered cells used are also different, the biological activities are uneven, the quality is unstable, and the yield is low. For example, the recombinant human DR5-Fc fusion protein (research reagent) sold by R&D systems has several amino acids different from other commercially available fusion protein drugs at the splicing site, the activity thereof is significantly reduced, the stability thereof is also poor, and different ratios of N-terminal splice variants are found. These all bring difficulty to subsequent process development and formulation of quality standards, and make it not suitable to be declared as a biological new drug.

SUMMARY

In view of the above, the present invention provides a novel sDR5-Fc recombinant fusion protein having high bioactivity and good stability.

The present invention provides a nucleotide sequence encoding an sDR5-Fc recombinant fusion protein, including:

a) a base sequence of SEQ ID NO: 1; or b) a sequence complementary to SEQ ID NO: 1; or c) a sequence encoding a protein having a same sequence as the protein encoded by the nucleotide sequence of a or b, but differing from the nucleotide sequence of a or b due to a degeneracy of a genetic code.

The present invention further provides an sDR5-Fc recombinant fusion protein encoded by the above nucleotide sequence (SEQ ID NO: 1).

The specific technical solutions are as follows.

An sDR5-Fc recombinant fusion protein having the amino acid sequence of SEQ ID NO: 2; or an sDR5-Fc recombinant fusion protein having an amino acid sequence of SEQ ID NO: 2, and having one or more substituted amino acids but without changing a biological active.

The present invention further provides applications of the above-mentioned sDR5-Fc recombinant fusion protein and the encoding nucleotide sequence thereof.

The specific technical solutions are as follows:

The above-mentioned nucleotide sequence is used for preparing a medicament for preventing and treating autoimmune hepatitis.

The above-mentioned nucleotide sequence is used for preparing a medicament for preventing and treating drug-induced liver injury.

The above-mentioned sDR5-Fc recombinant fusion protein is used for preparing a medicament for preventing and treating autoimmune hepatitis.

The above-mentioned sDR5-Fc recombinant fusion protein is used for preparing a medicament for preventing and treating drug-induced liver injury.

In some embodiments, the drug-induced liver injury is a liver injury induced by an antipyretic analgesic drug, a liver injury induced by an acetylcholinesterase inhibitor, or a liver injury induced by an anti-tuberculosis drug.

In some embodiments, the antipyretic analgesic drug is acetaminophen.

In some embodiments, the acetylcholinesterase inhibitor is tacrine.

In some embodiments, the anti-tuberculosis drug is isoniazid and/or rifampicin.

The present invention further provides an sDR5-Fc recombinant fusion protein having a same type of a protein encoded by SEQ ID NO: 2 but having different amino acid composition from the protein and an application thereof.

The specific technical solutions are as follows:

An sDR5-Fc recombinant fusion protein having an acid sequence of SEQ ID NO: 3, SEQ ID NO: 4, SEQ ID NO: 5 or SEQ ID NO: 6.

The above-mentioned sDR5-Fc recombinant fusion protein is used for preparing a medicament for preventing and treating autoimmune hepatitis.

The above-mentioned sDR5-Fc recombinant fusion protein is used for preparing a medicament for preventing and treating drug-induced liver injury.

The above-mentioned sDR5-Fc recombinant fusion protein and the nucleotide sequence thereof are used for preparing a medicament for preventing and treating autoimmune hepatitis or drug-induced liver injury. An administration route of the medicament includes any route capable of achieving a therapeutic effect, such as subcutaneous injection, intravenous injection, intramuscular injection, intraperitoneal injection, transdermal administration, etc.; and an administration dosage depends on severity of a disease, age of a patient, body weight, an administration mode, and an administration frequency.

The present invention further provides a pharmaceutical composition for preventing autoimmune hepatitis or drug-induced liver injury.

The specific technical solutions are as follows:

A pharmaceutical composition for preventing and treating autoimmune hepatitis, wherein the active ingredient thereof includes one or more of the above-mentioned sDR5-Fc recombinant fusion proteins.

A pharmaceutical composition for preventing and treating drug-induced liver injury, wherein the active ingredient thereof includes one or more of the above-mentioned sDR5-Fc recombinant fusion proteins.

In some embodiments, the pharmaceutical composition has a dosage form of injection.

In the present invention, through long-term research by the inventor, the protein gene sequence is reselected, and a high yield of sDR5-Fc protein (especially ZJ501-5) in CHO cells is achieved (the yield has reached 1.2 g/L, 500 L pilot scale production is completed). Moreover, the sDR5-Fc recombinant fusion protein (in particular, ZJ501-5) of the present invention has a bioactivity in vitro of 3-5 times higher than that of the sDR5-Fc product from R&D systems. The proportion of N-terminal splice variants is only 1% or less, and the stability of the protein medicament is high.

The sDR5-Fc recombinant protein (especially ZJ501-5) of the present invention can significantly improve the survival rate of mice having acute autoimmune hepatitis induced by Con A, which has potential application value in the treatment of human autoimmune liver diseases.

The sDR5-Fc recombinant fusion protein (especially ZJ501-5) of the present invention can significantly reduce serum transaminase levels, reduce liver pathological injury, reduce hepatocyte apoptosis rate and improve mouse survival rate in a variety of mouse drug-induced liver injury models (especially APAP-induced liver injury, tacrine-induced liver injury or isoniazid and rifampicin-induced liver injury).

The human sDR5-Fc fusion protein of the present invention blocks the binding between TRAIL and the DR5 receptor on the surface of the hepatocyte membrane by binding to the TRAIL molecule, thereby blocking hepatocyte apoptosis induced by the TRAIL-DR5 pathway. The TRAIL-DR5/DR4 pathway is the most important apoptotic pathway in the liver and is involved in many processes of liver injury caused by many factors. In drug-induced liver injury, regardless of the pathogenesis, it will eventually involve apoptosis of liver cells. Therefore, the indications of the medicament for treating drug-induced liver injury prepared by the sDR5-Fc recombinant fusion protein of the present invention are wider than that of the existing medicaments for treating drug-induced liver injury such as NAC, etc. Moreover, the human sDR5-Fc fusion protein of the present invention is a protein component derived from the human body, which is safer than existing medicaments such as NAC, etc. for treating drug-induced liver injury, and can be safely combined with other therapeutic agents to enhance efficacy and promote recovery.

The human sDR5-Fc fusion protein of the present invention is a novel drug candidate for preventing and treating drug-induced liver injury, and has wide therapeutic range, clear target, remarkable curative effect, high safety and great development potential.

DETAILED DESCRIPTION OF THE EMBODIMENTS

Figure 1:
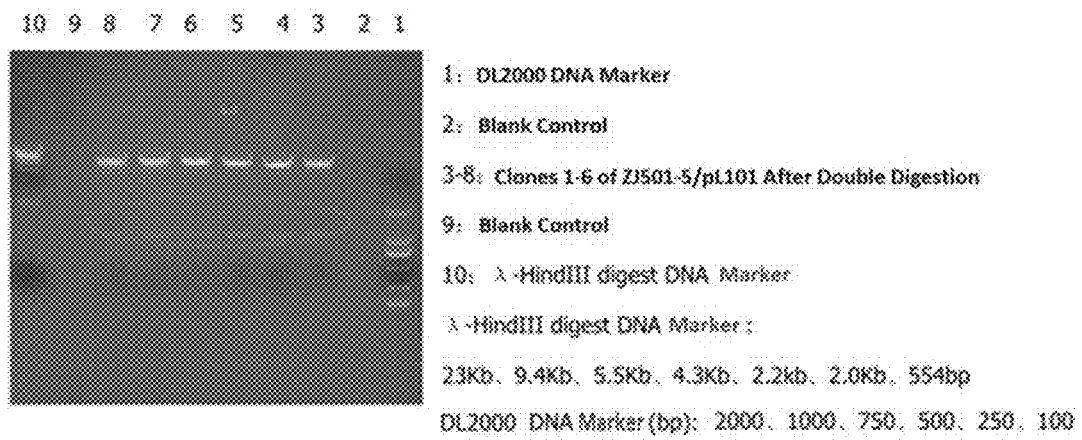
FIG. 1 is a diagram showing an agarose gel electrophoresis of a sDR5-Fc gene.

For ease of understanding, a more comprehensive description of the present invention is provided below with reference to the specific embodiments and the accompanying drawings. The present invention may be implemented in many different forms, which is not limited to the embodiments described herein. Rather, these embodiments are provided to help comprehensive understanding of the disclosure of the present invention.

The experimental methods in which the specific conditions are not specified in the following embodiments are generally performed according to the conventional conditions, such as the conditions described by Sambrook et al., Molecular cloning: a laboratory manual (New York: Cold Spring Harbor Laboratory Press, 1989), or according to the conditions recommended by the manufacturer. The various common chemical reagents used in the embodiments are commercially available products.

Unless otherwise defined, all technical and scientific terms used in the present invention have the same meaning as that commonly understood by those skilled in the art to which the present invention pertains. The terms used in the specification of the present invention are only for the purpose of describing the specific embodiments, and are not intended to limit the present invention. The term "and/or" in the present invention includes any and all combinations of one or more of the associated listed items.

Degeneracy of genetic code refers to the fact that several triplet genetic codes encoding the same amino acid are mostly identical in the first and second base position but different in the third base position. For example, ACU, ACC, ACA, ACG are all codons of threonine, and UGU, UGC, UGA, UGG are all codons of valine. Thus, if a point mutation occurs in the third base position of the codon, the species of the translated amino acid are not affected.

Autoimmune hepatitis refers to an inflammatory liver disease mediated by autoimmune response, clinical features thereof are elevated serum transaminases in varying degrees, hypergammaglobulinemia and positive autoantibodies, and histological features thereof are interface hepatitis infiltrated with lymphocyte and plasmacyte.

Drug-induced liver injury refers to liver injury induced by various prescription or over-the-counter chemical drugs, biological agents, traditional Chinese medicines, natural medicines, health care products, dietary supplements, and metabolites excipients thereof, etc.

In the present embodiment, the inventors performed fusions between human DR5 and Fc in various ways, and finally screened to obtain a sDR5-Fc recombinant fusion protein having an amino acid sequence of SEQ ID NO: 2, SEQ ID NO: 3, SEQ ID NO: 4, SEQ ID NO: 5, and SEQ ID NO: 6, named as ZJ501-5, ZJ501-1, ZJ501-2, ZJ501-3, and ZJ501-4, respectively.

In the present embodiment, the sDR5-Fc recombinant fusion protein has high stability and good bioactivity. Specifically, the HPLC purity of ZJ501-5 is about 99%, and the stability thereof is the best. Only a small amount of variants cut off one amino acid and two amino acids at the N-terminus appear, the ratio is 1.11%, and the variants cut off two amino acids at the N-terminus only account for about 0.11%.

In the experiment of blocking TRAIL-induced apoptosis, the bioactivity of ZJ501-5 was 3-5 times that of sDR5-Fc product of R&D systems.

In the present embodiment, the application of the above-mentioned sDR5-Fc recombinant fusion protein or a coding gene thereof in the preparation of a medicament for preventing and treating autoimmune hepatitis is provided.

The inventors modeled human autoimmune liver disease by using a Con A-induced mouse liver injury model, and studied the therapeutic effect of the sDR5-Fc recombinant fusion protein on Con A-induced acute autoimmune hepatitis. It was found that the sDR5-Fc recombinant fusion protein of the present invention was able to significantly reduce the transaminase level of Con A-induced mice, significantly improving the survival rate of mice, and ZJ501-5 had the best effect. Therefore, once the sDR5-Fc recombinant fusion proteins are applied to the preparation of a medicament for preventing and treating autoimmune hepatitis, ZJ501-5 is preferred.

In the present embodiment, the application of the sDR5-Fc recombinant fusion protein or a coding gene thereof in the preparation of a medicament for preventing and treating drug-induced liver injury is provided. The drug-induced liver injury especially refers to liver injury induced by an antipyretic analgesic drug, liver injury induced by an acetylcholinesterase inhibitor or liver injury induced by an anti-tuberculosis drug. Further, the antipyretic analgesic drug especially refers to acetaminophen; the acetylcholinesterase inhibitor especially refers to tacrine; and the anti-tuberculosis drug especially refers to isoniazid and/or rifampicin.

In the present embodiment, through APAP-induced liver injury, tacrine-induced liver injury, isoniazid and rifampicin-induced liver injury as experimental models, the inventors demonstrated that the sDR5-Fc recombinant fusion protein of the present invention can significantly reduce serum transaminase levels, reduce liver pathological injury, reduce hepatocyte apoptosis rate and improve mouse survival rate in a variety of mouse drug-induced liver injury models (especially APAP-induced liver injury, tacrine-induced liver injury or isoniazid and rifampicin-induced liver injury).

Further, the sDR5-Fc recombinant fusion protein applied for the preparation of the medicament for preventing and treating drug-induced liver injury is preferably ZJ501-5.

The sDR5-Fc recombinant fusion protein of the present invention may be prepared into a corresponding pharmaceutical composition or pharmaceutical preparation together with a conventional excipient (e.g., a protein protectant, a pH adjusting agent, an osmotic pressure adjusting agent, etc.) in the medicament.

An administration route of the medicament includes any route capable of achieving a therapeutic effect, such as subcutaneous injection, intravenous injection, intramuscular injection, intraperitoneal injection, transdermal administration, etc.; and an administration dosage depends on severity of a disease, age of a patient, body weight, an administration mode, and an administration frequency.

Further, the dosage form of the pharmaceutical composition or pharmaceutical preparation is preferably an injection. The injection is an injection prepared by adding the sDR5-Fc recombinant fusion protein as an active ingredient, an auxiliary material used for injection and sterilizing water used for injection. The auxiliary material includes a pH adjusting agent, an osmotic pressure adjusting agent, a solubilizing agent, etc.; the pH adjusting agent includes hydrochloric acid, citric acid, sodium hydroxide, ammonium hydroxide, sodium citrate, disodium hydrogen phosphate, sodium dihydrogen phosphate, etc.; the osmotic pressure adjusting agent includes sodium chloride, glucose, etc.; and the solubilizing agent includes tween, hydroxypropyl-β-cyclodextrin, etc.

Further, the contents of various components in the injection are: sDR5-Fc recombinant fusion protein 0.1 mg/ml-200 mg/ml, osmotic pressure adjusting agent 0.1-100 mg/ml, pH adjusting agent 0.1-20 mg/ml, and solubilizing agent 0.1-10 mg/ml.

The sDR5-Fc recombinant fusion protein and the pharmaceutical composition thereof may be applied in combination with existing hepatitis drugs: For example, in combination with N-acetylcysteine, a drug that treats APAP-induced liver injury, or in combination with compound glycyrrhizin tablets and silybin, drugs that treat liver disease, both of the combinations have synergistic treatment effects.

The following are the specific embodiments.

Embodiment 1: Design and Recombination of Recombinant Human DR5-FC Expression Sequences Accumulating through long-term experience, the inventors constructed a recombinant fusion protein and performed fusions between human DR5 and Fc in various ways. The results of mass spectrum showed that, for most of the target proteins, eleven amino acids (ITQQDLAPQQR; SEQ ID NO: 7) were cut at N-terminal. In order to express the target protein having relatively uniform N-terminal, the fusion protein with a common signal peptide where the intermediate linker sequence and the 18 amino acids at N-terminal were deleted was finally obtained, named as sDR5-Fc (ZJ501-5). The plasmid was transiently transfected, and the expressed supernatant was purified and then subjected to mass spectrometry and activity analysis.

The DNA sequence of ZJ501-5 is:

(SEQ ID NO: 1)
ATGGGTGTACTGCTCACACAGAGGACGCTGCTCAGTCTGGTCCTTGCACTC

CTGTTTCCAAGCATGGCGAGCATGTCCAGCCCCTCAGAGGGATTGTGTCC

ACCTGGACACCATATCTCAGAAGACGGTAGAGATTGCATCTCCTGCAAAT

ATGGACAGGACTATAGCACTCACTGGAATGACCTCCTTTTCTGCTTGCGCT

GCACCAGGTGTGATTCAGGTGAAGTGGAGCTAAGTCCCTGCACCACGACC

AGAAACACAGTGTGTCAGTGCGAAGAAGGCACCTTCCGGGAAGAAGATT

CTCCTGAGATGTGCCGGAAGTGCCGCACAGGGTGTCCCAGAGGGATGGTC

AAGGTCGGTGATTGTACACCCTGGAGTGACATCGAATGTGTCCACAAAGA

AGAGCCCAAATCTTGTGACAAAACTCACACATGCCCACCGTGCCCAGCAC

CTGAACTCCTGGGGGACCGTCAGTCTTCCTCTTCCCCCCAAAACCCAAG

GACACCCTCATGATCTCCCGGACCCCTGAGGTCACATGCGTGGTGGTGGA

CGTGAGCCACGAAGACCCTGAGGTCAAGTTCAACTGGTACGTGGACGGCG

TGGAGGTGCATAATGCCAAGACAAAGCCGCGGGAGGAGCAGTACAACAG

CACGTACCGTGTGGTCAGCGTCCTCACCGTCCTGCACCAGGACTGGCTGA

ATGGCAAGGAGTACAAGTGCAAGGTCTCCAACAAAGCCCTCCCAGCCCCC

ATCGAGAAAACCATCTCCAAAGCCAAAGGGCAGCCCCGAGAACCACAGG

TGTACACCCTGCCCCCATCCCGGGATGAGCTGACCAAGAACCAGGTCAGC

-continued
CTGACCTGCCTGGTCAAAGGCTTCTATCCCAGCGACATCGCCGTGGAGTG

GGAGAGCAATGGGCAGCCGGAGAACAACTACAAGACCACGCCTCCCGTG

CTGGACTCCGACGGCTCCTTCTTCCTCTACAGCAAGCTCACCGTGGACAAG

AGCAGGTGGCAGCAGGGGAACGTCTTCTCATGCTCCGTGATGCATGAGGC

TCTGCACAACCACTACACGCAGAAGAGCCTCTCCCTGTCTCCGGGTAAAT

GA

The amino acid sequence of ZJ501-5 is:

(SEQ ID NO: 2)
MGVLLTQRTLLSLVLALLFPSMASMSSPSEGLCPPGHHISEDGRDCISCK

YGQDYSTHWNDLLFCLRCTRCDSGEVELSPCTTTRNTVCQCEEGTFREED

SPEMCRKCRTGCPRGMVKVGDCTPWSDIECVHKEEPKSCDKTHTCPPCPA

PELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEA

LHNHYTQKSLSLSPGK

The gene sequence of sDR5-Fc (ZJ501-5) was linked to a pL101 eukaryotic expression vector by conventional techniques such as enzyme digestion, ligation, etc., and identified by double digestion with Hind3 and EcoRI. Agarose gel electrophoresis showed a target fragment of about 1300 bp and a pL101 vector fragment of about 9 kb. After the vector was constructed, the results were confirmed by double enzyme digestion, as shown in FIG. 1.

Figure 2:
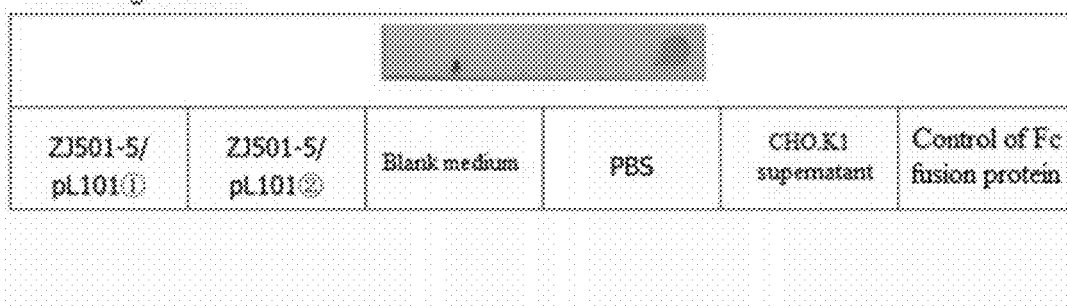
FIG. 2 is a diagram showing a Dot Blot assay of a DR5-Fc recombinant fusion protein (ZJ501-5)

Embodiment 2: Detections of Expression and Physicochemical Properties of Human sDR5-Fc Recombinant Protein The plasmid sDR5-Fc/pL101 was transiently transfected into CHO.K1 cells with Lipofectamine2000, and the supernatant was collected after 48 hours for Dot Blot assay. The results were positive as shown in FIG. 2.

The CHO.K1-S cells were recovered, resuspended into 10 ml recovered CHO.K1-S cells with $5 \times 10^5$ cells/ml, and cultured in serum-free medium of FreeStyle™ CHO Expression Medium added with Glutamine having a final concentration of 8 mmol/L. The culture was performed in a 37° C. 8% $CO_2$ shaking incubator at 120 rpm. When the number of cells was greater than $1 \times 10^6$/ml, the cells were passaged, and the medium was added to the culture to 30 ml, and the number of cells is maintained at $2-5 \times 10^5$/ml. For subsequent passages, the cell density was maintained at $2-5 \times 10^5$/ml in each passage, and the CHO.K1-S cells needed to be subjected to more than three passages.

On the day before transfection, the CHO.K1-S cells were adjusted to have a cell density of $5-6 \times 10^5$/ml after being shaken and counted. 100 ml of the adjusted CHO.K1-S cells was placed in the 37° C. 8% C02 shaking incubator for culture at 120 rpm, and transfection was performed the next day.

On the day of transfection, the CHO.K1-S cells were counted and the viability was calculated. The cell density should be $1.2-1.5 \times 10^6$/ml and the viability is more than 95%. The cell density was adjusted to $1 \times 10^6$/ml, and the cells with 30 ml/part was added to the 100 ml shake flask for next step.

FreeStyle™ MAX Reagent was gently inverted and mixed four times. Then 37.5 μl of the Free Style™ MAX Reagent was added to 0.6 ml OPTIpro™ SFM diluent, and 37.5 μg of the plasmid was added to the 0.6 ml OPTIpro™ SFM diluent as well. Both were mixed evenly, and the mixture was kept in stationary culture at room temperature for 10-20 min.

The mixture after being incubated was added to the shake flask with the prepared CHO.K1-S cells, and cultured in the 37° C. 8% C02 shaking incubator at 120 rpm for 7 days. The product was purified by affinity column and then subjected to SDS-PAGE, SEC-HPLC and mass spectrometry.

The steps of the mass spectrometry:
1. First perform buffer exchange of the sample into 50mNH4FA (pH 6.6) and measure the concentration thereof;
2. Digest each sample with Ides;
3. Add DTT to reduce the disulfide bond; and
4. Inject the sample and perform mass spectrometry analysis.

Figure 3:
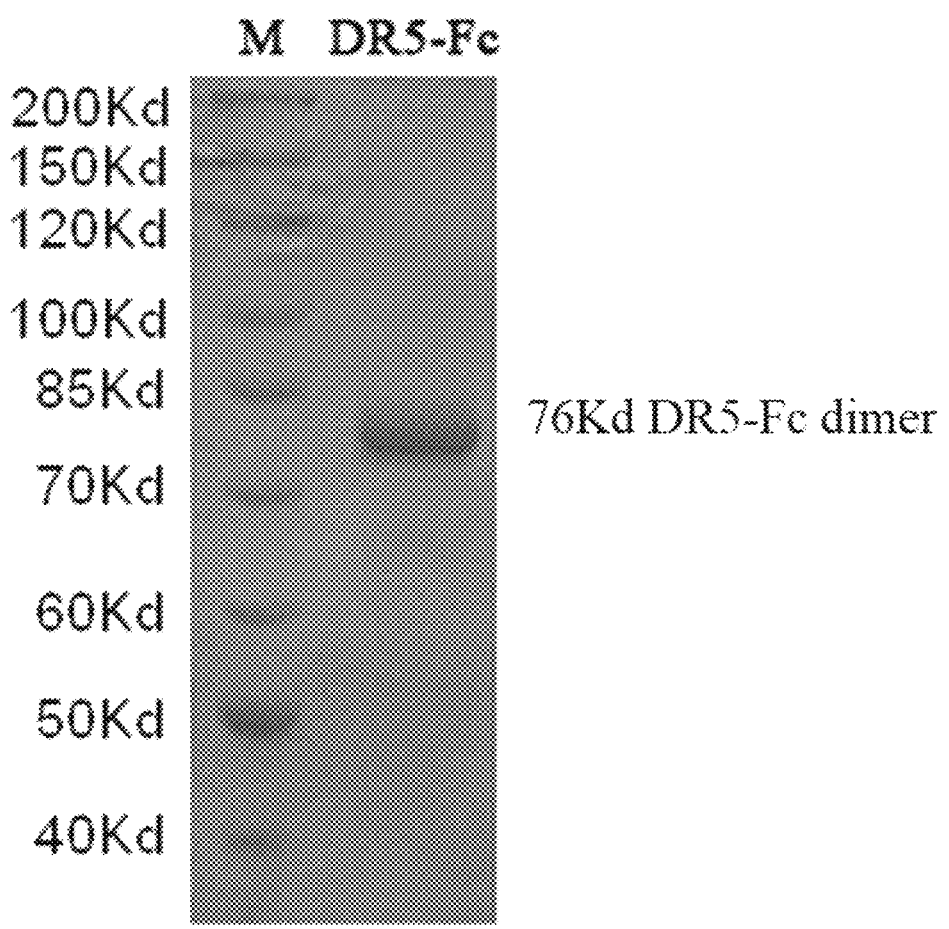
FIG. 3 is an 8% SDS-PAGE non-reduced electropherogram.
Figure 4:
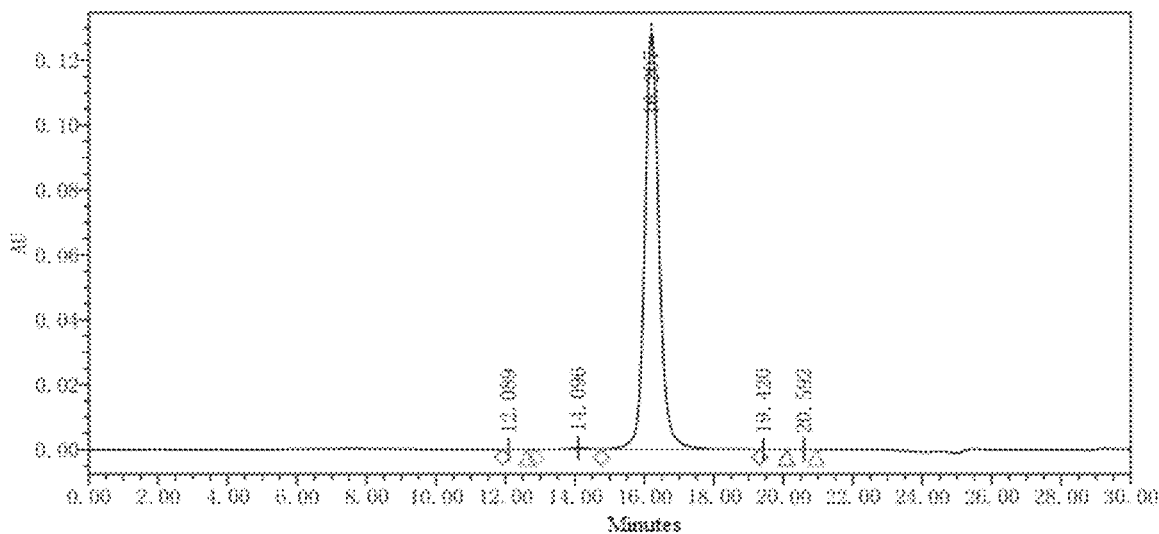
FIG. 4 is a diagram showing a SEC-HPLC analysis of ZJ501-5 after purification.
Figure 5:
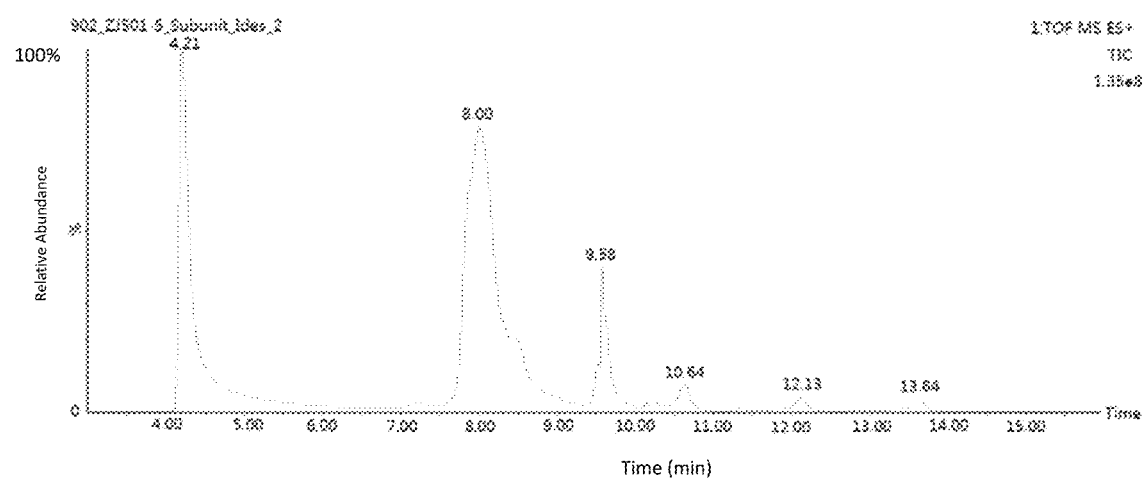
FIG. 5 is a TIC diagram of ZJ501-5 after reduction.
Figure 6:
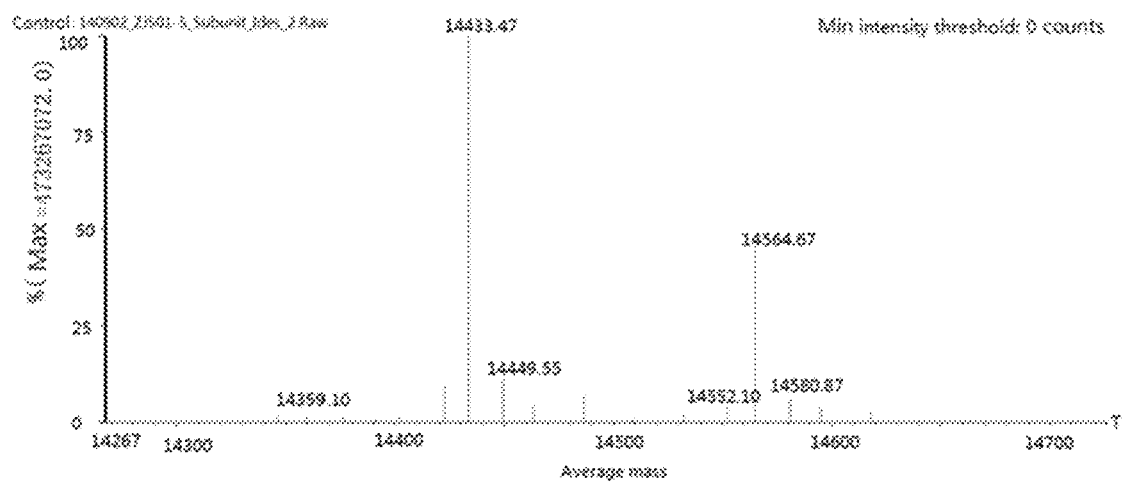
FIG. 6 is a mass spectrum of ZJ501-5 data processed with Biopharmalynx software.

Referring to SDS-PAGE (FIG. 3), SEC-HPLC of ZJ501-5 after purification (FIG. 4) (protein purity is up to 99.47%), TIC of ZJ501-5 after reduction (FIG. 5) and mass spectrum of the ZJ501-5 data processed with Biopharmalynx software (FIG. 6), the ratio of N-terminal splice variants was analyzed according to FIG. 5 and FIG. 6. Referring to the following table, M (O) represented that an additional methionine appeared at the N-terminus of the corresponding protein and was oxidized, and S-S represented a disulfide bond. O represented the first amino acid was oxidized. And after introducing FIG. 5 and FIG. 6 into the database, the results of the variants cut off one amino acid at the N-terminus and the variants cut off two amino acids at the N-terminus were obtained.

The Ratio of N-terminal Splice Variants Shown in the Following Table

| Splice Variants and Modifier Types | Detected Molecular Weight | Ratio |
| --- | --- | --- |
| ZJ501-5+M (O) | 14580.8701 | 3.43% |
| ZJ501-5+M | 14564.6738 | 25.59% |
| ZJ501-5+M (S-S) | 14552.1016 | 2.13% |
| ZJ501 (O) | 14449.5449 | 6.23% |
| ZJ501 | 14433.4688 | 56.19% |
| ZJ501 (S-S) | 14421.9883 | 5.43% |
| Cut Off One Amino Acid at N-terminus | 14346.2637 | 1% |
| Cut Off Two Amino Acids at N-terminus | 14261.3359 | 0.11% |

The results showed that the purity of ZJ501-5 reached 99%, and only a small amount of variants cut off one amino acid or two amino acids at the N-terminus, the ratio is 1.11%. The variants cut off two amino acids at the N-terminus only account for about 0.11%.

ZJ501-5 was a target protein with relatively uniform N-terminus obtained by removing the N-terminal unstable sequence based on ZJ501-1, ZJ501-2, ZJ501-3 or ZJ501-4 protein. The ratios of the N-terminal splice variants of ZJ501-1, ZJ501-2, ZJ501-3, ZJ501-4, ZJ501-5 proteins were shown in the following table.

| Sample Name | Temperature | N-terminal Splice Variants % |
| --- | --- | --- |
| ZJ501-1 | 37° C. | 31.35 |
| ZJ501-2 | 37° C. | 34.72 |
| ZJ501-3 | 37° C. | 48.69 |
| ZJ501-4 | 37° C. | 51.66 |
| ZJ501-5 | 37° C. | 1.11 |

From the above, the drug stability of ZJ501-5 protein is the highest.

The sequences of ZJ501-1, ZJ501-2, ZJ501-3, ZJ501-4 proteins are as follows:

ZJ501-1
(SEQ ID NO: 3)
MEQRGQNAPAASGARKRHGPGPREARGARPGPRVPKTLVLVVAAVLLLVS

AESALITQQDLAPQQRAAPQQKRSSPSEGLCPPGHHISEDGRDCISCKYG

QDYSTHWNDLLFCLRCTRCDSGEVELSPCTTTRNTVCQCEEGTFREEDSP

EMCRKCRTGCPRGMVKVGDCTPWSDIECVHKEGSSNTKVDKKVEPKSCDK

THTCPPCPAPELLGGPSVFLEPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNV

FSCSVMHEALHNHYTQKSLSLSPGK

ZJ501-2
(SEQ ID NO: 4)
MEQRGQNAPAASGARKRHGPGPREARGARPGPRVPKTLVLVVAAVLLLVS

AESALITQQDLAPQQRAAPQQKRSSPSEGLCPPGHHISEDGRDCISCKYG

QDYSTHWNDLLFCLRCTRCDSGEVELSPCTTTRNTVCQCEEGTFREEDSP

EMCRKCRTGCPRGMVKVGDCTPWSDIECVHKEEPKSCDKTHTCPPCPAPE

LLGGPSVELEPPKPKDTLMISRTPEVTCVVVDVSHEDPEVKFNWYVDGVE

VHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALH

NHYTQKSLSLSPGK

ZJ501-3
(SEQ ID NO: 5)
MGVLLTQRTLLSLVLALLFPSMASMITQQDLAPQQRAAPQQKRSSPSEGL

CPPGHHISEDGRDCISCKYGQDYSTHWNDLLFCLRCTRCDSGEVELSPCT

TTRNTVCQCEEGTFREEDSPEMCRKCRTGCPRGMVKVGDCTPWSDIECVH

KEEPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQV

SLTCLVKGFYPSDIAVEWESNGQPENNYKTTPPVLDSDGSFFLYSKLTVD

KSRWQQGNVFSCSVMHEALHNHYTQKSLSLSPGK

ZJ501-4 Amino AcidSequence (Signal Peptide-Target Sequence)
(SEQ ID NO: 6)
MGVLLTQRTLLSLVLALLFPSMASMAAPQQKRSSPSEGLCPPGHHISEDG

RDCISCKYGQDYSTHWNDLLFCLRCTRCDSGEVELSPCTTTRNTVCQCEE

GTFREEDSPEMCRKCRTGCPRGMVKVGDCTPWSDIECVHKEEPKSCDKTH

-continued

TCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFS

CSVMHEALHNHYTQKSLSLSPGK

Embodiment 3: Detection of Bioactivity of ZJ501-5

(1) Establishing Detection Method of Killing Activity of Commercial Trail

Jurkat cells during logarithmic growth phase were collected, resuspended with 10% FCS RPMI-1640/DMEM after being counted, adjusted to a cell density of $8\times10^4$/ml, added to a 96-well cell culture plate at 100 L/well, and placed in a 37° C. 8% C02 incubator to culture for 20-24 h.

The commercial Trail was resuspended in the above complete culture medium containing actinomycin D (final concentration 0.03 µg/ml) at a final concentration of 500-1000 ng/ml. The commercial Trail was diluted with the complete culture medium containing actinomycin D at a ratio of 1:2 in a gradient dilution method and a total of 15-20 concentration gradients were obtained. The diluted samples were added into a 96-well cell culture plate at 100 ul/well, and cultured in the incubator for 18-22 h. Then, a freshly prepared mixed MTS/PMS coloring solution with a ratio of 20 to 1 was added into the 96-well cell culture plate at 20 µL/well, and cultured in the incubator for 3-4 h. The A490-A630 value was measured with a microplate reader.

Figure 7:
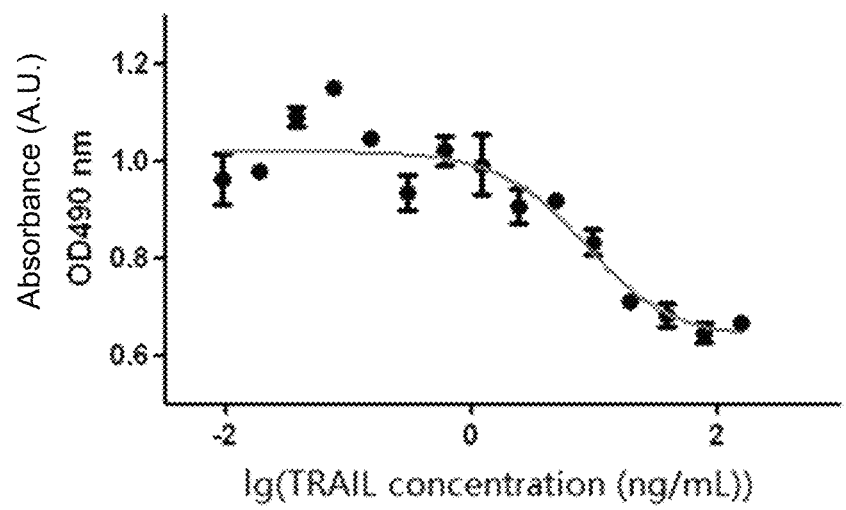
FIG. 7 is a standard curve for a detection of killing activity of a commercial Trail.

M5 analysis software was used to fit the standard curve: the concentration of the sample was used as the abscissa, and the A490-A630 value was used as the ordinate. A 4-parameter equation regression model was selected, and the curve had a reversed S shape. The software automatically calculated out an EC50 of 8.382 ng/ml and an EC90 of 27.65 ng/ml. (See FIG. 7)

(2) Establishing Detection Method of Bioactivity of Commercial DR5-FC Fusion Protein;

Jurkat cells during logarithmic growth phase were collected, resuspended with 10% FCS RPMI-1640/DMEM after being counted, adjusted to a cell density of $8\times10^4$/ml, added to a 96-well cell culture plate at 100 µL/well, and placed in a 37° C. 8% C02 incubator to culture for 20-24 h.

EC90 of the killing activity of the commercial Trail was calculated, a Trail with a final concentration of EC90 was added to the above complete culture medium containing actinomycin D (final concentration 0.03 µg/ml). The commercial DR5-Fc (R&D Systems) was diluted with the above complete culture medium containing actinomycin D and Trail of EC90 at a ratio of 1:1 to obtain a solution having a concentration of 10 ng/ml. The solution was diluted with the medium at a ratio of 1:2 in a gradient dilution method, and 15 concentration gradients were obtained. The diluted samples were added to the 96-well cell culture plate at 100 µl/well, and cultured in the medium for 18-22 h.

Then, the freshly prepared mixed MTS/PMS coloring solution with a ratio of 20 to 1 was added to the 96-well cell culture plate at 20 µL/well, and cultured in the incubator for 3-4 h. The A490-A630 value was measured with a microplate reader.

Figure 8:
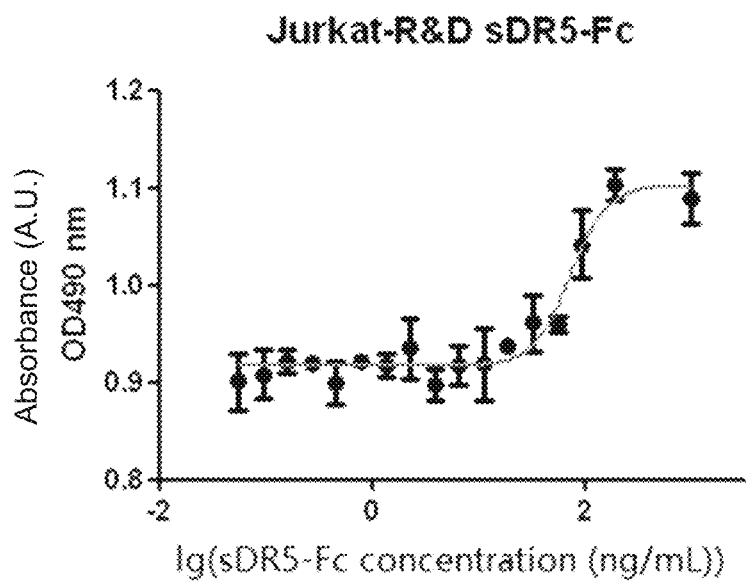
FIG. 8 is a standard curve of a bioactivity detection for a commercial DR5-FC fusion protein.

The results of the bioactivity detection of the commercial DR5-Fc fusion protein (R&D systems): M5 analysis software was used to fit the standard curve: the concentration of the sample was used as the abscissa, the A490-A630 value was used as the ordinate, a 4-parameter equation regression model was selected, and the curve had a positive S shape. Three different experiments were performed to compare the variation of EC50. The EC50 is 71.82 ng/ml. (See FIG. 8)

(3) Detection Method of Bioactivity and Relative Activity of ZJ501-5

The method is the same as (2), the sample is ZJ501-5 (SEQ ID NO: 2), and the reference substance is commercial DR5-Fc (R&D systems company). The experiment was performed three times by two different operators, respectively, and the relative bioactivity of the ZJ501-5 was calculated for each experiment: relative bioactivity (%)=commercial DR5-Fc EC50/sample DR5-Fc EC50× 100%. Variations of different operators and experimental batches were compared.

Figure 9:
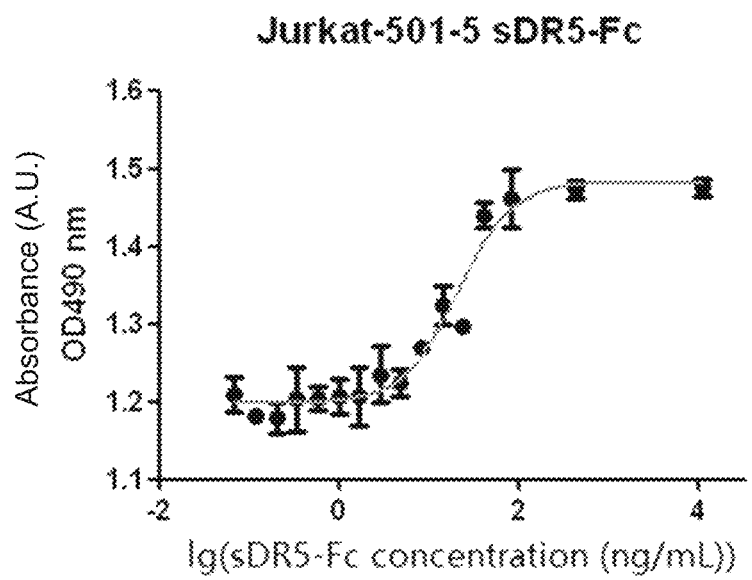
FIG. 9 is a standard curve of a bioactivity detection for ZJ501-5.

The results of the bioactivity and relative activity of the ZJ501-5 of the present invention: on average, ZJ501-5 EC50 was 20.25 ng/ml, the commercial DR5-Fc EC50 was 71.82 ng/ml, and the relative bioactivity of the ZJ501-5 was 355%. (See FIG. 9).

Embodiment 4: sDR5-Fc Blocks TRAIL-Induced Hepatocyte Apoptosis

The method was the same as (1) and (2) of embodiment 3, the target cells were HepG2 cells, the sample was ZJ501-5 (SEQ ID NO: 2), and the reference substance was commercial DR5-Fc (R&D systems).

Figure 10:
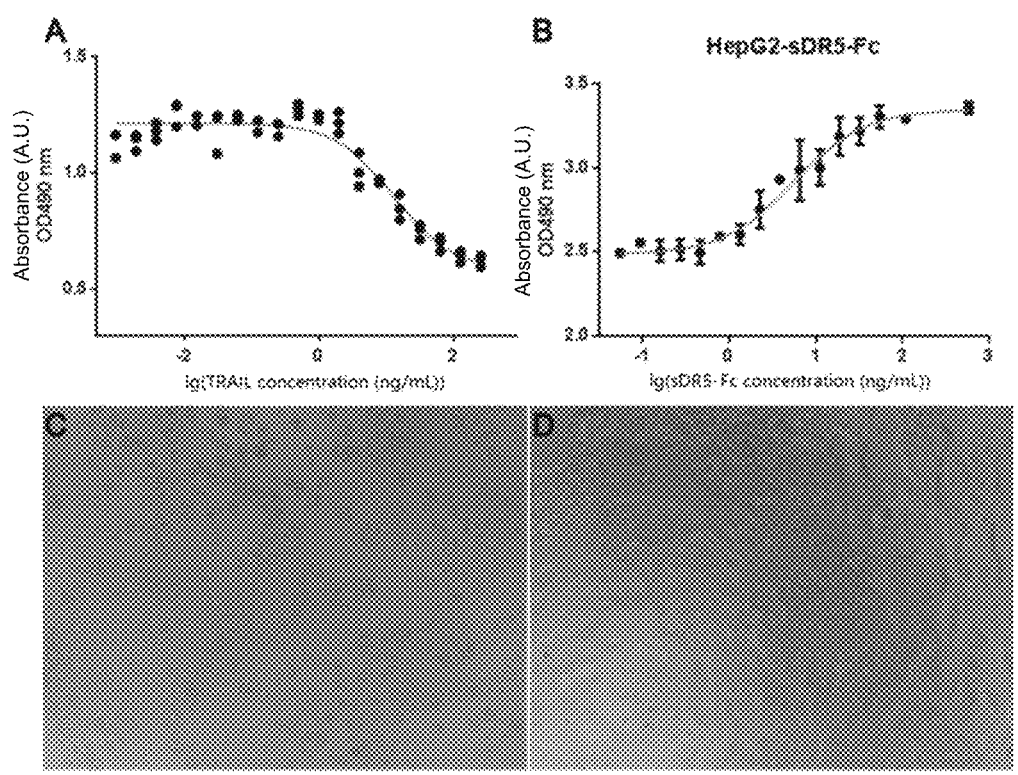
FIG. 10 is a schematic diagram showing results of blocking TRAIL-induced hepatocyte apoptosis by the human sDR5-Fc recombinant fusion protein in embodiment 4; A is results of apoptosis of HepG2 cells induced by different concentrations of TRAIL; B is results of blocking TRAIL-induced apoptosis of HepG2 cells by different concentrations of the human sDR5-Fc recombinant fusion protein; C is a morphological diagram of HepG2 cells after apoptosis induced by TRAIL; and D is a morphological diagram of HepG2 cells after TRAIL-induced apoptosis blocked by the human sDR5-Fc recombinant fusion protein.

The experiment found that (See FIG. 10) that the human sDR5-Fc recombinant fusion protein can effectively block TRAIL-induced hepatocyte apoptosis. Moreover, the bioactivity of the ZJ501-5 (EC50=5.7 ng/ml) in HepG2 cells was nearly 5 times that of the sDR5-Fc protein of the R&D systems (EC50=27.6 ng/ml).

Embodiment 5: Treatment of Con A-Induced Mouse Autoimmune Hepatitis by sDR5-Fc

The pathological process of Con A-induced mouse liver injury model is similar to the pathological process of various acute and chronic liver diseases, especially the pathological features of specific liver injury induced by activation of T lymphocytes, which can well simulate the pathogenic process of human autoimmune liver diseases.

Experiment 1

Thirty-six male C57BL/6 mice, aged 6 to 8 weeks, were randomly divided into 6 groups, 6 mice in each group. The 6 groups included a model control group, sDR5-Fc treatment groups (27 mg/kg, 9 mg/kg, 3 mg/kg and 1 mg/kg) and a positive control group (silibinin 27 mg/kg), respectively. Each mouse was intraperitoneally injected with PBS, 27 mg/kg of sDR5-Fc (ZJ501-5 of the present invention), 9 mg/kg of sDR5-Fc, 3 mg/kg of sDR5-Fc, 1 mg/kg of sDR5-Fc, and 27 mg/kg of silibinin, and the injection volumes thereof were all 20 m/kg. After 1 h, each mouse was injected with 17 mg/kg of Con A into the tail vein at a volume of 10 ml/kg. The blood was collected from the tail vein at 8 h and 24 h after injection of Con A. At 48 h, each mouse was sacrificed with C02, the blood was collected from the heart, and the liver was collected, embedded in paraffin after being fixed in 4% PFA, sectioned, and stained with HE. TUNEL staining of the liver tissue sections was performed using a DeadEnd Fluorometric TUNEL System (Promega, G3250) kit. Immunohistochemical staining of the liver tissue sections was performed by using TRAIL antibody (Santa Cruz, sc-6079). The blood of the mice was placed at room temperature for 1 h, and centrifuged at 3000 rpm at 4° C. for 10 min. The upper serum was separated, and ALT and AST detection kits from Nanjing Jiancheng Biotechnology Research Institute Co., Ltd. were used to detect the liver function of ALT and AST.

Figure 11:
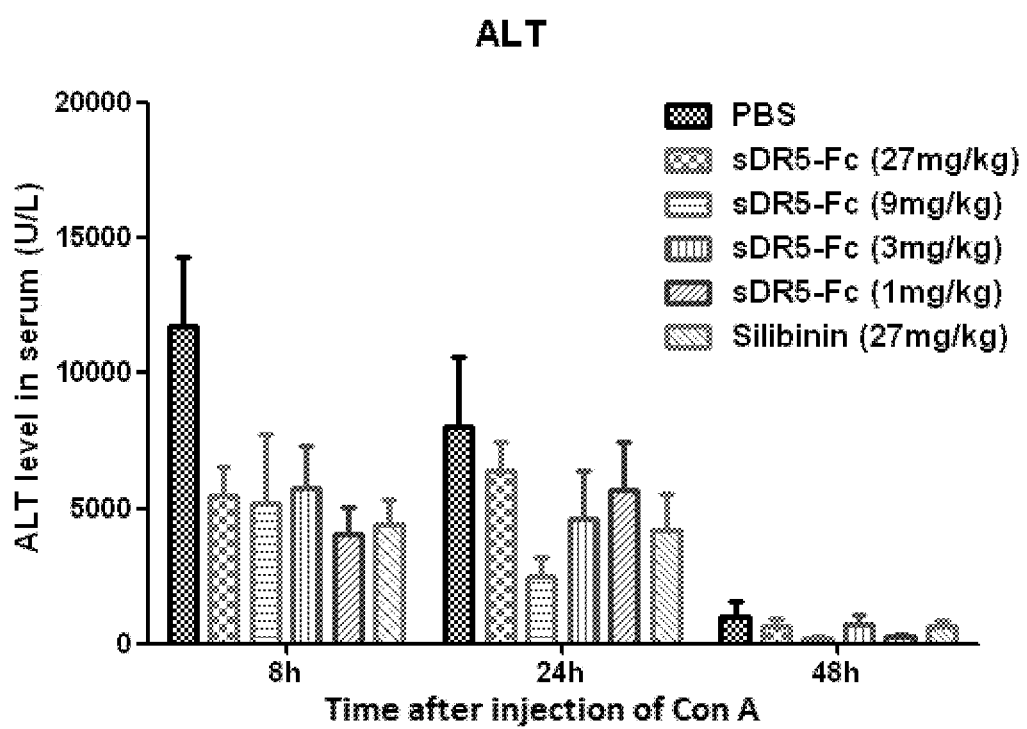
FIG. 11 is a schematic diagram showing results of ALT liver function test in the mouse liver injury model experiment in embodiment 5.
Figure 12:
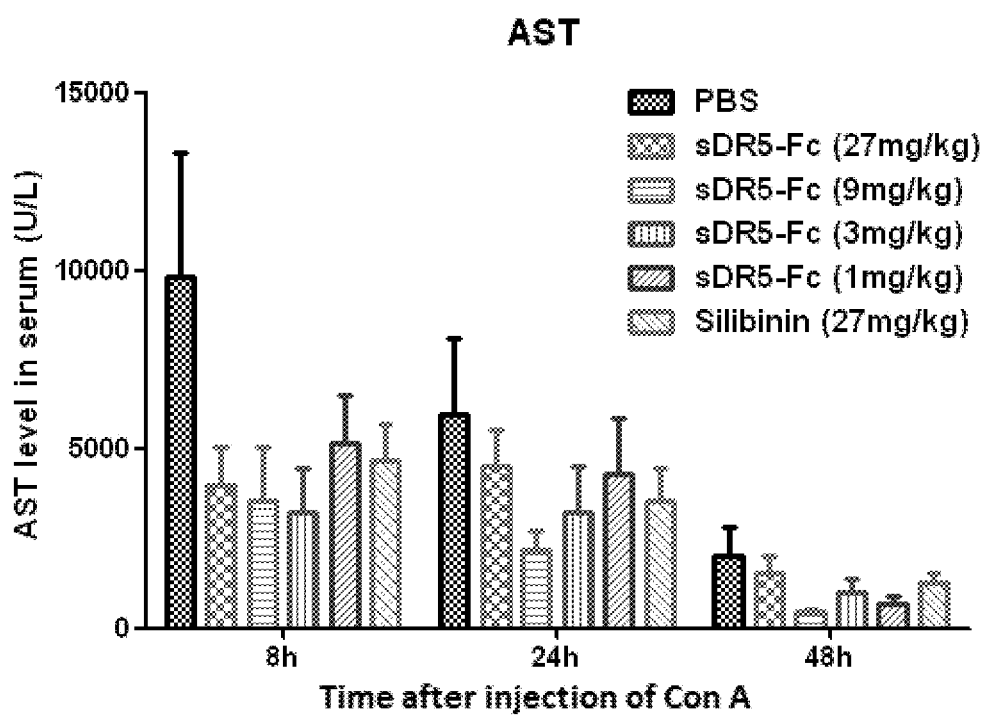
FIG. 12 is a schematic diagram showing results of AST liver function test in the mouse liver injury model experiment in embodiment 5.
Figure 13:
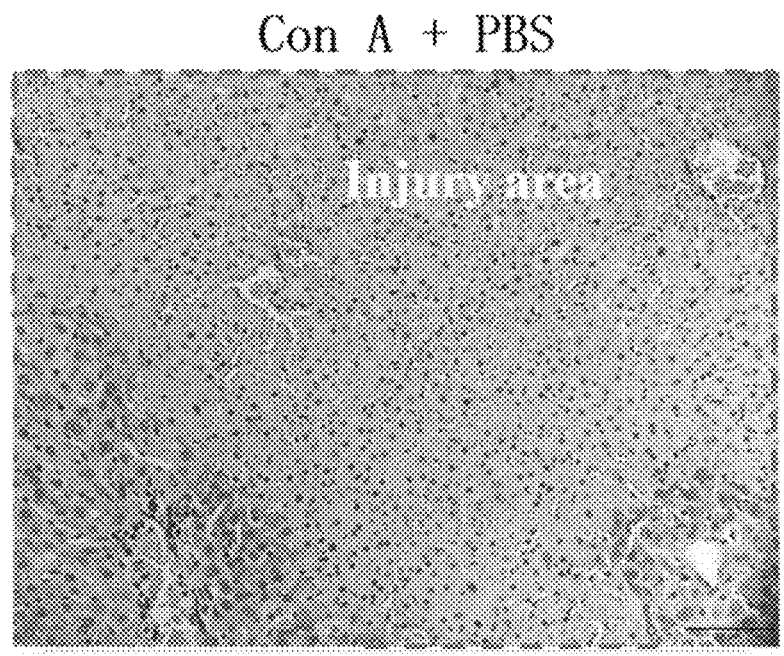
FIG. 13 is a schematic diagram showing results of a control group with HE staining in the mouse liver injury model experiment in embodiment 5.
Figure 14:
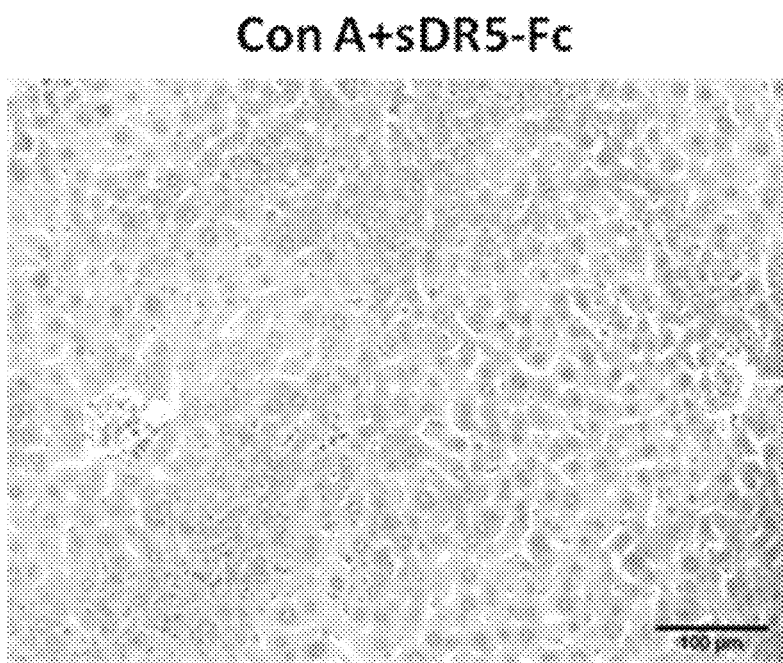
FIG. 14 is a schematic diagram showing results of a sDR5-Fc with HE staining in the mouse liver injury model experiment in embodiment 5.
Figure 15:
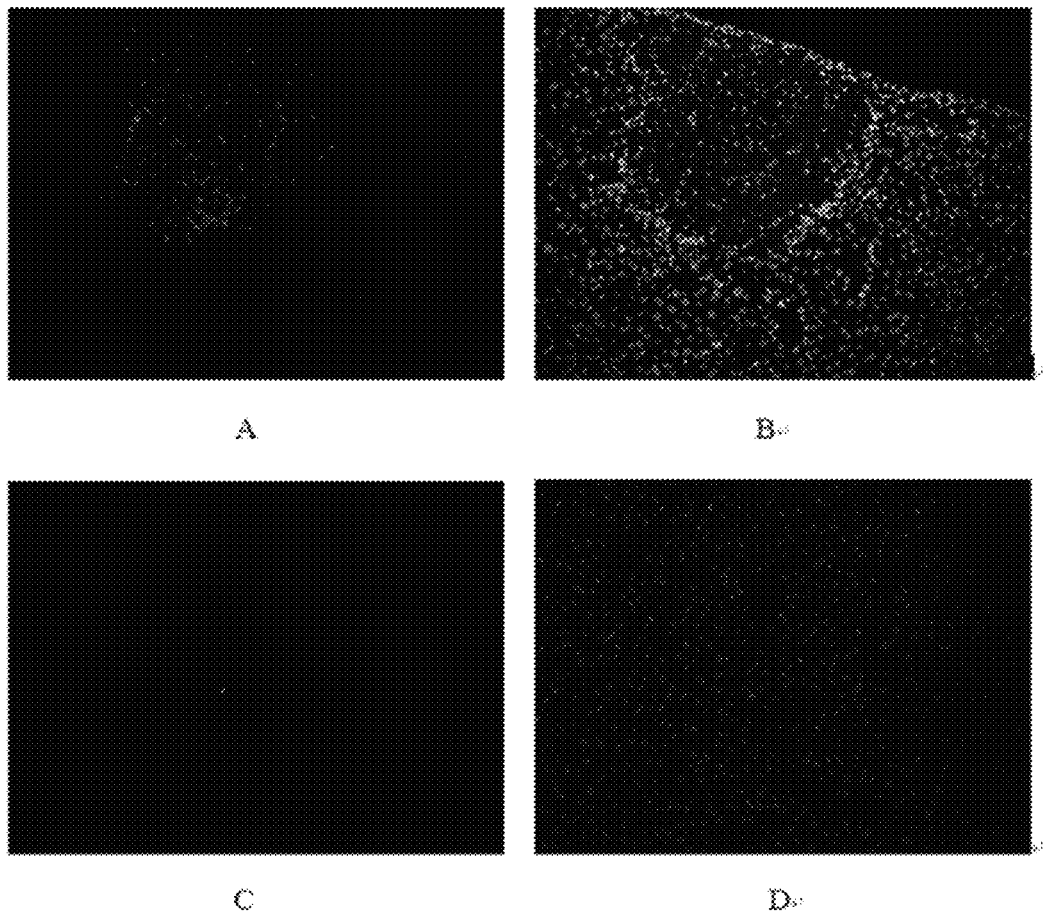
FIG. 15 is a schematic diagram showing results of TUNEL staining of liver tissue sections in embodiment 5; A is results of TUNEL staining of the liver tissue of mice in the Con A model group; B is a result of DAPI staining; C is results of TUNEL staining of liver tissue of mice treated with 9 mg/kg sDR5-Fc (501-5); and D is a result of DAPI staining.
Figure 16:
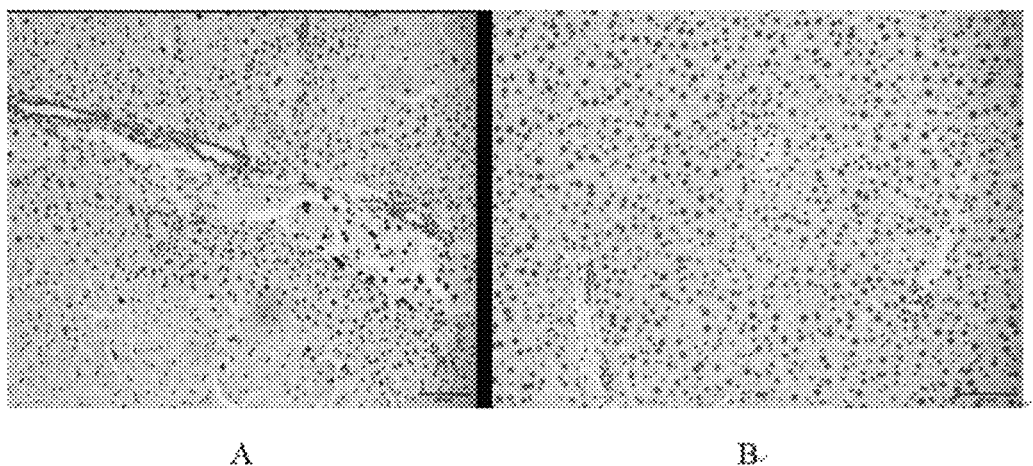
FIG. 16 is a schematic diagram showing results of TRAIL immunohistochemical staining in liver tissue sections in embodiment 5; A shows results of TRAIL immunohistochemical staining of liver tissue of mice in the Con A model group; and B shows results of TRAIL immunohistochemical staining in liver tissue of mice treated with 9 mg/kg sDR5-Fc (501-5).

Experimental results: see FIGS. 11-16. FIG. 11 and FIG. 12 showed that intraperitoneal injection of 9 mg/kg sDR5-Fc could treat Con A-induced acute hepatitis in mice, mainly showed that the sDR5-Fc could significantly reduce the serum transaminase level. FIG. 13 and FIG. 15 (two drawings in the top row) showed that a large area of hepatocyte death occurred in the liver tissue at 48 h after injection of Con A. FIG. 14 and FIG. 15 (two drawings in the bottom row) showed that at 48 h after the mice were injected intraperitoneally with 9 mg/kg sDR5-Fc and induced by Con A, most of the hepatocytes survived, there were few apoptotic hepatocytes, and the liver tissue was intact. FIG. 16 showed that after intravenous injection of Con A in mice, a large number of TRAIL positive lymphocytes were recruited to the liver tissue, thus triggering a large amount of TRAIL-DR5-mediated hepatocyte apoptosis, however, after treatment with 9 mg/kg sDR5-Fc (ZJ501-5) on the mice, few TRAIL positive lymphocytes were recruited to liver tissue because the sDR5-Fc blocked TRAIL from binding to DR5 on the surface of the hepatocytes, therefore, the induced hepatocyte apoptosis was also less.

Experimental conclusion: The sDR5-Fc of the present invention can significantly inhibit the elevation of transaminase in serum in the acute hepatitis mouse model, inhibit the pathological changes of the liver, and play a significant liver-protecting effect. In the dose-dependent experiment, 9 mg/kg of sDR5-Fc for intraperitoneal injection is the optimal dose.

Experiment 2

Fifty-six male C57BL/6 mice, aged 6 to 8 weeks, were randomly divided into 7 groups, 8 mice in each group. The 7 groups included a blank control group, a model control group, and model administration groups (respectively administrated with the sDR5-Fc proteins having the gene sequences of No. 1 to No. 5, specifically SEQ ID NO: 3-SEQ ID NO: 6, SEQ ID NO: 2, at 10 mg/kg). Each mouse was injected with PBS and 10 mg/kg of sDR5-Fc proteins of No. 1 to No. 5 into the tail vein at an injection volume of 10 ml/kg, respectively. After 1 h, each mouse was injected with Con A at 15 mg/kg in the tail vein at an injection volume of 10 ml/kg. At 8 h after injection of Con A, the blood was collected from the submandibular vein of each mouse, the blood of the mice was placed at room temperature for 1 h, and centrifuged at 3000 rpm at 4° C. for 10 min. The upper serum was separated, and ALT, AST and albumin detection kits from Nanjing Jiancheng Biotechnology Research Institute Co., Ltd. were used to detect the levels of ALT, AST and albumin.

Figure 17:
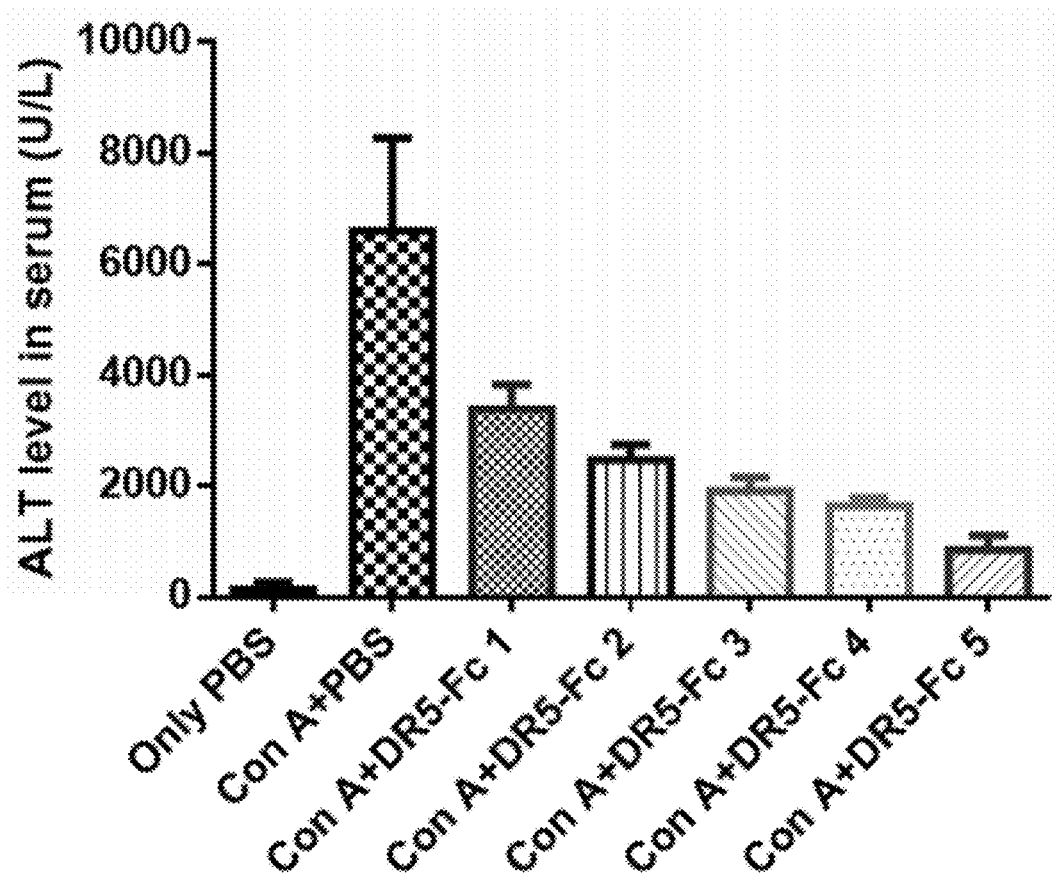
FIG. 17 is a schematic diagram showing results of detection of ALT levels in serum in embodiment 5.
Figure 18:
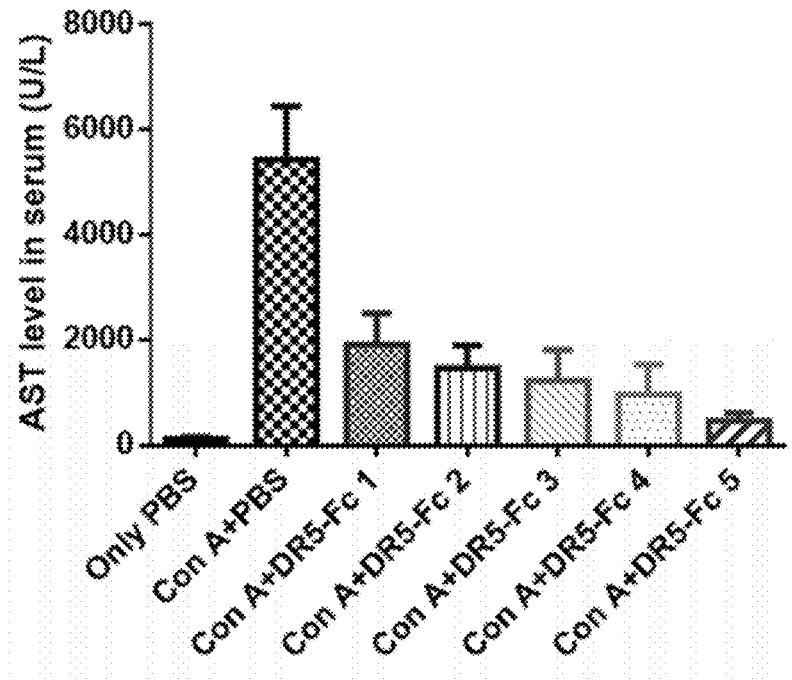
FIG. 18 is a schematic diagram showing results of detection of AST levels in serum in embodiment 5.
Figure 19:
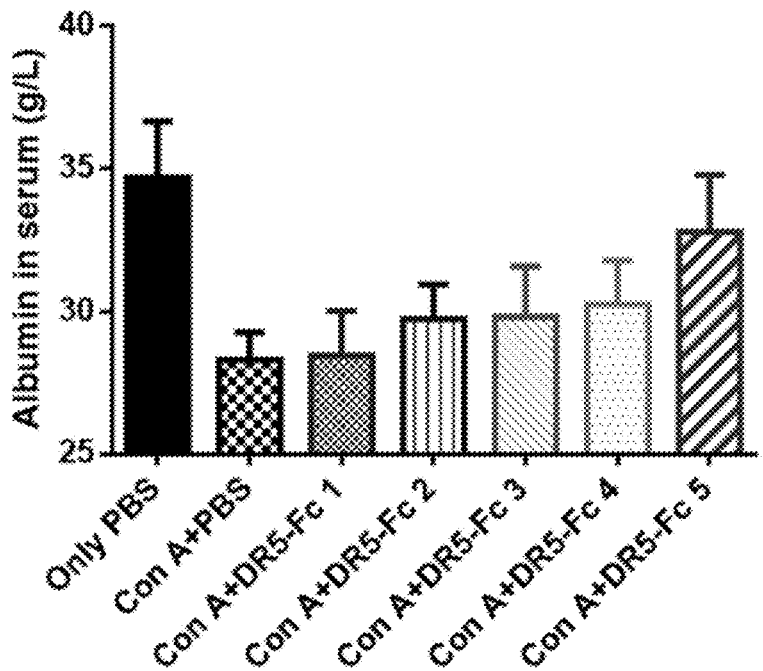
FIG. 19 is a schematic diagram showing results of detection of albumin levels in serum in embodiment 5.

Experimental results: see FIGS. 17-19.

Experimental conclusion: The sDR5-Fc (ZJ501-5) of the present invention can significantly reduce the transaminase level in Con A-induced mouse hepatitis relative to the sDR5-Fc proteins encoded by other gene sequences (FIGS. 17 and 18). At the same dose, the sDR5-Fc protein with the ZJ501-5 sequence had a better therapeutic effect, showing better liver function and being capable of synthesizing more serum albumin to be secreted into the blood (FIG. 19).

Experiment 3

Figure 20:
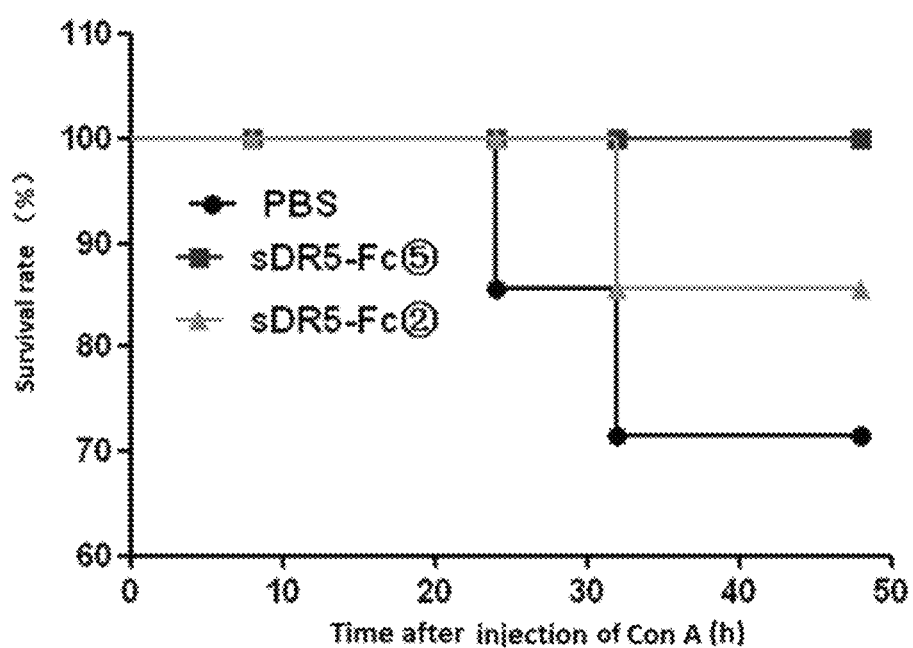
FIG. 20 is a schematic diagram showing survival curves of the mice in embodiment 5.

Twenty-one male C57BL/6 mice, aged 6 to 8 weeks, were randomly divided into 3 groups, 7 mice in each group. The 3 groups included a model control group, sDR5-Fc with No. 2 gene sequence (ZJ501-2) treatment group at 32.2 mg/kg, sDR5-Fc (ZJ501-5) with No. 5 gene sequence treatment group at 21.6 mg/kg. Each mouse was injected with PBS, 32.2 mg/kg of sDR5-Fc with No. 2 gene sequence (ZJ501-2), and 21.6 mg/kg of sDR5-Fc5 with No. 5 gene sequence (ZJ501-5) in the tail vein, respectively, and injection volumes thereof were all 20 ml/kg. After 1 h, each mouse was injected with Con A at 15 mg/kg in the tail vein at an injection volume of 10 m/kg. The survival of the mice was observed within 48 h after the injection of Con A, and the survival curve was drawn as shown in FIG. 20.

Experimental conclusion: The sDR5-Fc (ZJ501-5) of the present invention can significantly improve the survival rate of mice with acute autoimmune hepatitis induced by Con A, and the sDR5-Fc protein having the ZJ501-5 gene sequence at a dose of 21.6 mg/kg has a better therapeutic effect than the sDR5-Fc protein having the ZJ501-2 gene sequence at a dose of 32.2 mg/kg.

Embodiment 6: Treatment of APAP-Induced Liver Injury by sDR5-Fc (1) Forty C57BL/6 male mice were divided into 4 groups (a saline group, a 0.1 mg/kg sDR5-Fc group, a 1 mg/kg sDR5-Fc group and a 10 mg/kg sDR5-Fc group, and the sDR5-Fc was the ZJ501-5 of the present invention), 10 mice in each group. Each mouse was administered intragastrically with 400 mg/kg APAP. After 1 h, each group of mice was injected intraperitoneally with saline, 0.1 mg/kg sDR5-Fc, 1 mg/kg sDR5-Fc, and 10 mg/kg sDR5-Fc at an administration volume of 10 ml/kg, respectively. The blood was collected from the submandibular vein of each mouse at 6 h, 24 h, 32 h and 48 h after the administration of APAP, the serum was separated and serum transaminase levels were detected. The mice were sacrificed at 48 h, and parts of the livers were fixed in 4% PFA, embedded in paraffin, sectioned, HE stained, TUNEL stained, and TRAIL immunohistochemical stained.

Figure 21:
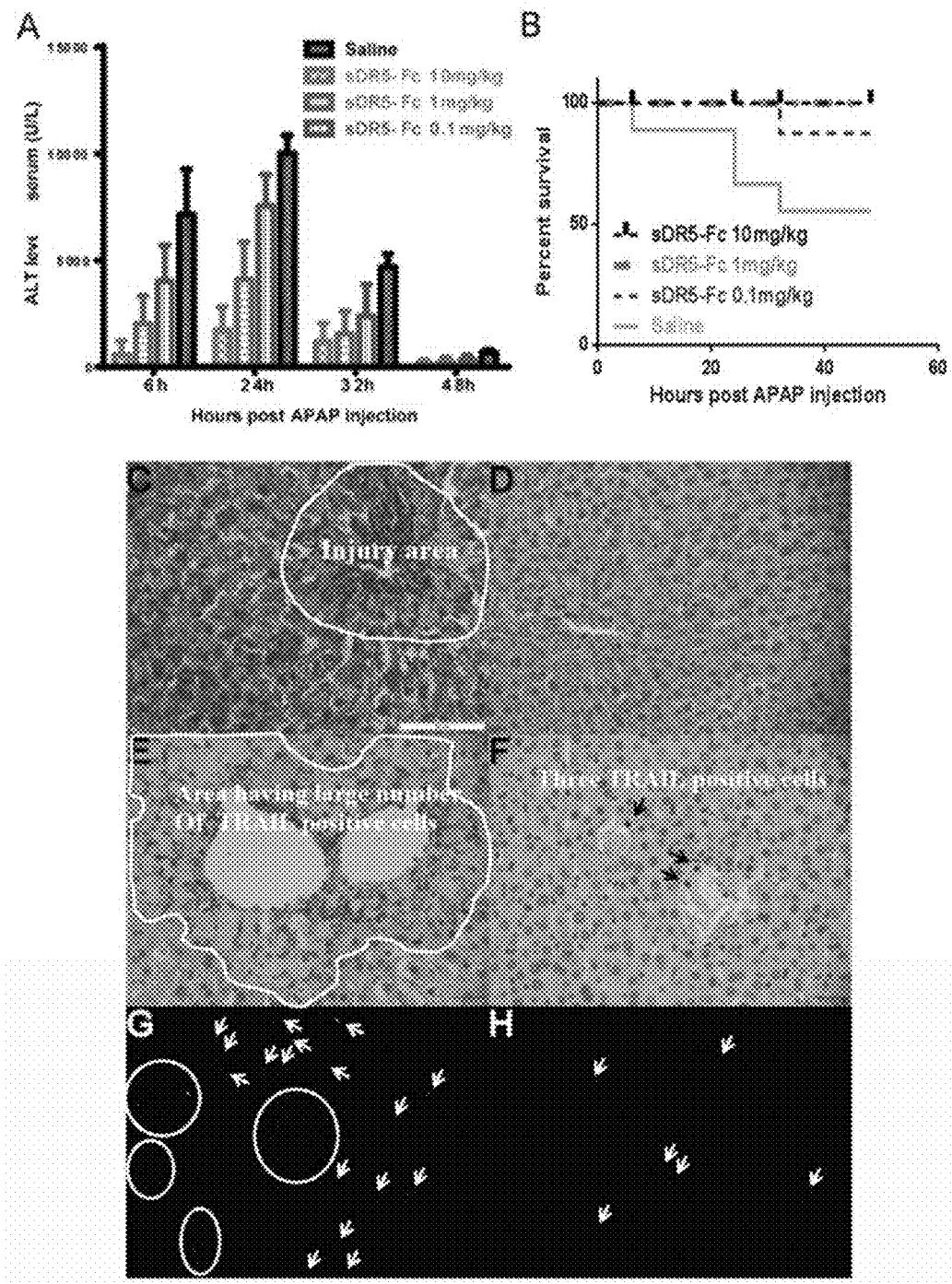
FIG. 21 is a schematic diagram showing results of a treatment on mice with APAP-induced liver injury by the human sDR5-Fc recombinant fusion protein in embodiment 6; A shows serum transaminase levels reduced by different doses of human sDR5-Fc in an APAP-induced mouse liver injury model; B shows survival rates of mice improved by different doses of human sDR5-Fc in an APAP-induced mouse liver injury model; C shows liver tissue sections of mice in a saline group; D shows liver tissue sections of mice in 10 mg/kg SDR5-Fc group; E shows results of TRAIL immunohistochemical staining of liver tissue sections of mice in the saline group; F shows results of TRAIL immunohistochemical staining of liver tissue sections of mice in the 10 mg/kg sDR5-Fc group; G shows results of TUNEL staining of liver tissue sections of mice in the saline group; and H shows results of TUNEL staining of liver tissue sections of mice in the 10 mg/kg sDR5-Fc group.

The results showed that (see FIG. 21): 10 mg/kg sDR5-Fc recombinant fusion protein could significantly reduce serum transaminase levels in APAP-induced liver injury mice (Fig. A). Meanwhile, it could be seen that the mice in the saline group showed significant liver pathological injury (Fig. C, the area in the white circle was the liver injury area, and a large number of liver cells were apoptotic). The liver tissue sections of the 10 mg/kg sDR5-Fc group were basically normal (Fig. D). A large number of TRAIL-positive lymphocytes infiltrated in the liver tissue sections of the mice in the saline group (Fig. E, the area in the white circle was a large number of TRAIL-positive cells), while there was almost no TRAIL-positive lymphocyte infiltration in the liver tissue sections of the mice of the 10 mg/kg sDR5-Fc group (Fig. F, black arrows pointed to the TRAIL-positive cells). In the saline group, there were a large number of TUNEL-positive cells in the liver tissue sections (Fig. G, the area in the white circles and white arrows pointed to TUNEL-positive cells), while in the 10 mg/kg sDR5-Fc group, there were almost no TUNEL-positive cells in the liver tissue sections (Fig. H, white arrows pointed to TUNEL-positive cells). Therefore, the 10 mg/kg sDR5-Fc recombinant fusion protein was able to alleviate liver pathological injury in mice, reduce the number of apoptotic hepatocytes, and decrease the number of TRAIL-positive infiltrating lymphocytes.

(2) Forty C57BL/6 male mice were divided into 4 groups (a saline group, a 0.1 mg/kg sDR5-Fc group, a 1 mg/kg sDR5-Fc group and a 10 mg/kg sDR5-Fc group, and the sDR5-Fc was the ZJ501-5 of the present invention), 10 mice in each group. Each mouse was administered intragastrically with 500 mg/kg APAP. After 1 h, each group of mice were injected intraperitoneally with saline, 0.1 mg/kg of sDR5-Fc, 1 mg/kg of sDR5-Fc, and 10 mg/kg of sDR5-Fc at an administration volume of 10 mi/kg, respectively. The survival rates of the mice were observed at 6 h, 24 h, 32 h and 48 h after the administration of APAP.

The results showed that (see Fig. B in FIG. 21): The 10 mg/kg sDR5-Fc recombinant fusion protein significantly increased the survival rate of the mice with the APAP-induced liver injury.

Embodiment 7: Treatment of sDR5-Fc Synergized with NAC on APAP-Induced Liver Injury Forty C57BL/6 male mice were divided into 4 groups (a saline group, a 10 mg/kg sDR5-Fc group, a 100 mg/kg NAC group, and 10 mg/kg sDR5-Fc and 100 mg/kg NAC combined drug group, and the sDR5-Fc was the ZJ501-5 of the present invention), 10 mice in each group. Each mouse was administered intragastrically with 500 mg/kg APAP After 1 h, each group of mice were injected intraperitoneally with saline, 10 mg/kg of sDR5-Fc, 100 mg/kg of NAC, and a combination of 10 mg/kg of sDR5-Fc and of 100 mg/kg NAC at an administration volume of 10 ml/kg, respectively. The blood was collected from the submandibular veins of each mouse at 24 h after the administration of APAP, the serum was separated, and serum transaminase levels were detected.

Figure 22:
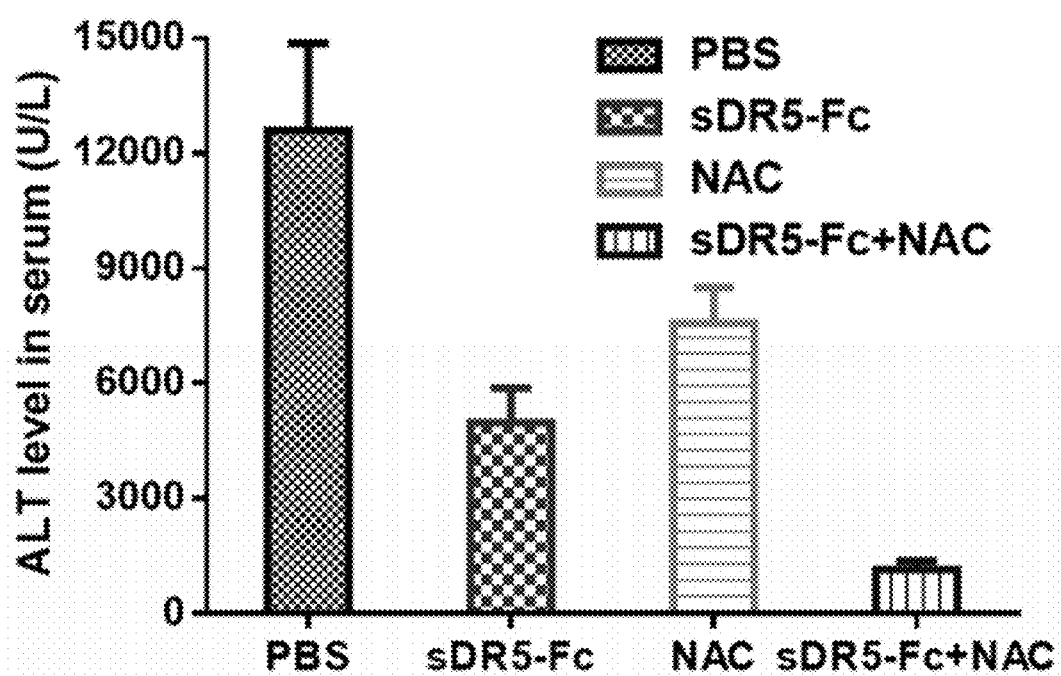
FIG. 22 is a schematic diagram showing a result of a treatment on APAP-induced liver injury by cooperating the human sDR5-Fc recombinant fusion protein with NAC in embodiment 7.

The results showed that (see FIG. 22): The 10 mg/kg sDR5-Fc recombinant fusion protein and 100 mg/kg NAC had a synergistic effect to significantly reduce serum transaminase levels in the mice with the APAP-induced liver injury.

Embodiment 8: Treatment of sDR5-Fc on Tacrine-Induced Liver Injury (1) Thirty BALB/c female mice were divided into 3 groups (a saline group, a 10 mg/kg sDR5-Fc group (ZJ501-5), and a 10 mg/kg silymarin group), 10 mice in each group. Each mouse was intragastrically administered with 25 mg/kg of tacrine. After 1 h, each group of mice were administrated with normal saline (intravenous injection), 10 mg/kg of sDR5-Fc (intravenous injection), and 10 mg/kg of silymarin (intragastric administration) at an administration volume of 10 ml/kg, respectively. The blood was collected from the submandibular veins of each mouse at 6 h after the administration of the tacrine, serum was separated, and serum transaminase levels were detected.

The results showed that (see FIG. 23): The 10 mg/kg sDR5-Fc recombinant fusion protein significantly reduced serum transaminase levels in the mice with tacrine-induced liver injury.

(2) Thirty BALB/c female mice were divided into 3 groups (a saline group, a 10 mg/kg sDR5-Fc group (ZJ501-5), and a 10 mg/kg silymarin group), 10 mice in each group. Each mouse was intragastrically administered with 30 mg/kg of tacrine. After 1 h, each group of mice were administrated with normal saline (intravenous injection), 10 mg/kg of sDR5-Fc (intravenous injection), and 10 mg/kg of silymarin (intragastric administration) at an administration volume of 10 ml/kg, respectively. The survival rates of the mice were observed at 6 h, 24 h, 32 h and 48 h after the administration of the tacrine.

Figure 23:
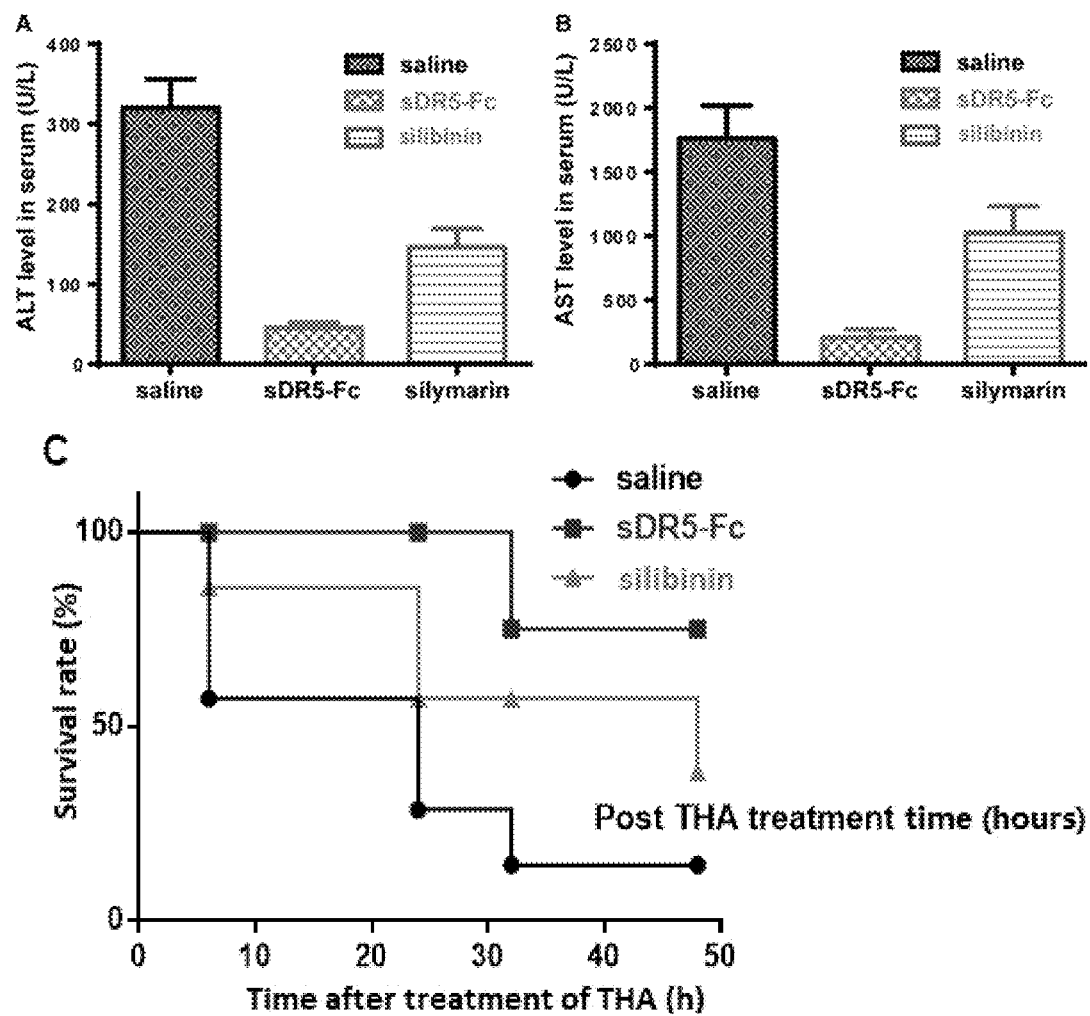
FIG. 23 is a schematic diagram showing results of treatments on tacrine-induced liver injury in mice by the human sDR5-Fc recombinant fusion protein in embodiment 8; A and B show reduction of serum transaminase levels by 10 mg/kg sDR5-Fc recombinant fusion protein in a tacrine-induced mouse liver injury model; and C shows survival rates of mice improved by 10 mg/kg sDR5-Fc recombinant fusion protein in the tacrine-induced mouse liver injury model.

The results showed that (see FIG. 23). The 10 mg/kg sDR5-Fc recombinant fusion protein significantly increased the survival rate of the mice with the tacrine-induced liver injury.

Embodiment 9: Treatment of sDR5-Fc on Isoniazid and Rifampicin-Induced Liver Injury (1) Thirty BALB/c female mice were divided into 3 groups (a saline group, a 10 mg/kg sDR5-Fc group (ZJ501-5), and a 10 mg/kg silymarin group), 10 mice in each group. Each mouse was intragastrically administered with 100 mg/kg of isoniazid and 150 mg/kg of rifampicin once a day, and continuous administration was performed for 2 weeks. One hour after the administration on the first day of each week, each group of mice were respectively administrated with normal saline (intravenous injection), 10 mg/kg of sDR5-Fc (intravenous injection), and 10 mg/kg of silymarin (intragastric administration) at an administration volume of 10 ml/kg, respectively, which was performed once a week. The blood was collected from the submandibular veins of each mouse at 8 h after the last administration of the isoniazid and rifampicin, serum was separated, and serum transaminase levels were detected.

Figure 24:
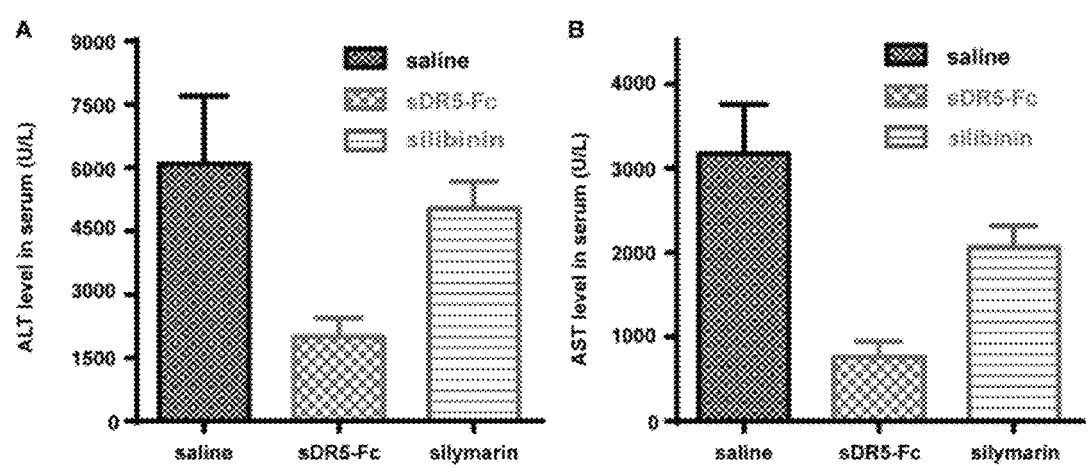
FIG. 24 is a schematic diagram showing results of treatments on isoniazid and rifampicin-induced liver injury in mice by the human sDR5-Fc recombinant fusion protein in embodiment 9.

The results showed (see FIG. 24): 10 mg/kg sDR5-Fc significantly reduced serum transaminase levels in the mice with the soniazid and rifampicin-induced liver injury.

Embodiment 10: Study on the Maximum Tolerated Dose of sDR5-Fc

Twenty BALB/c female mice were divided into two groups (a solvent group and a 2198.4 mg/kg sDR5-Fc group (ZJ501-5)), 10 mice in each group. Each mouse of the solvent group was intravenously injected with a volume of 40 ml/kg of the solvent each time, and each mouse of the sDR5-Fc group was intravenously injected with 2198.4 mg/kg of the sDR5-Fc recombinant fusion protein each time. After observation for 7 days, the mice were sacrificed, serum was separated after blood collection from the heart, and liver functions (including ALT, AST, TP, ALB, Tbil levels) were detected. The liver, spleen, kidney, and lung were observed and weighed. After the liver was fixed, paraffin embedding, sectioning, and HE staining were performed.

Figure 25:
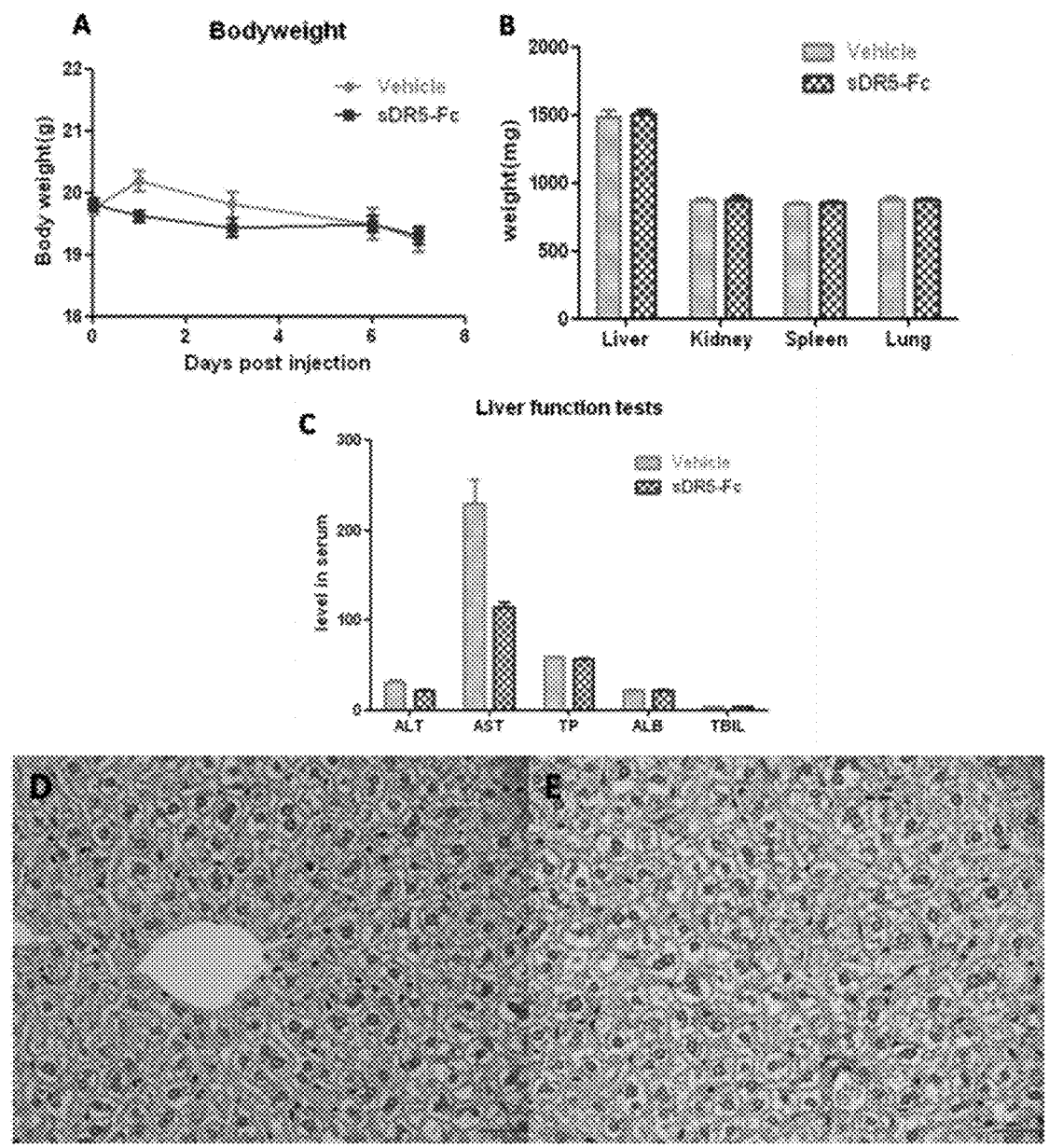
FIG. 25 is a schematic diagram showing a result of a maximum tolerated dose experiment of the human sDR5-Fc recombinant fusion protein in embodiment 10; after a mouse is intravenously injected with 2198.4 mg/kg sDR5-Fc recombinant fusion protein or a same volume of a solvent, A is a diagram showing a change of body weight of the mouse in one week after an injection, B is a diagram showing a weight comparison of liver, kidney, spleen and lung of the mouse in one week after the injection, C is a diagram showing a comparison of liver function of the mouse in one week after the injection, and D and E show results of HE staining of liver tissue sections of the mouse in one week after an injection with the solvent (Fig. D) or sDR5-Fc (Fig. E).

The results showed (see FIG. 25): One time of intravenous injection of 2198.4 mg/kg sDR5-Fc recombinant fusion protein did not cause death in mice. After 7 days of administration, no differences in the average body weight, the liver, kidney, spleen, and lung between the mice of the solvent group and the mice of the sDR5-Fc group were found, and no toxicity was observed. The detection of the liver function in serum showed that the liver functions of the two groups of mice were basically normal, and the serum transaminase levels of the mice in the sDR5-Fc group were lower than that in the solvent group. The liver tissue sections of the two groups of mice also showed that liver structures were normal. The hepatocytes were radially arranged around the central vein to form a cell plate with a single-unit-cell thickness. Therefore, the maximum tolerated dose of sDR5-

Fc in mice was greater than 2198.4 mg/kg, and the safe dose range of the sDR5-Fc medicament was large.

The technical features of the above-described embodiments may be arbitrarily combined. To simplify the description, all possible combinations of the technical features in the above embodiments are not described. However, as long as the combination of these technical features has no contradiction, it should be considered as within the scope of the present specification.

The above-mentioned embodiments only show several implementation modes of the present invention, the description of which is relatively specific and detailed, but it cannot be understood as limitations to the scope of the present invention. It should be noted that a number of variations and improvements may be made by those skilled in the art without departing from the inventive concept of the present invention, which still fall in the protection scope of the present invention. Therefore, the scope of the present invention should be determined by the claims attached.

What is claimed is:

1. A soluble death receptor 5-fragment crystallizable (sDR5-Fc) recombinant fusion protein, having the amino acid sequence of SEQ ID NO: 2.

2. A soluble death receptor 5-fragment crystallizable (sDR5-Fc) recombinant fusion protein having the amino acid sequence of SEQ ID NO: 3, SEQ ID NO: 5 or SEQ ID NO: 6.

3. A pharmaceutical composition for treating autoimmune hepatitis or drug-induced liver injury, wherein, an active ingredient thereof comprises an sDR5-Fc recombinant fusion protein having the amino acid sequence of SEQ ID NO: 2, SEQ ID NO: 3, SEQ ID NO: 5 or SEQ ID NO: 6.

4. The pharmaceutical composition of claim 3, wherein, a dosage form of the pharmaceutical composition is an injection.

5. A nucleotide sequence encoding the sDR5-Fc recombinant fusion protein of claim 1, comprising:
a) a base sequence of SEQ ID NO: 2.

6. A method of treating autoimmune hepatitis in a subject, the method comprising administering a medicament comprising the sDR5-Fc recombinant fusion protein of claim 1 as an essential ingredient in the medicament, wherein the medicament is administered in a therapeutically effective amount to treat autoimmune hepatitis.

7. A method of treating drug-induced liver injury in a subject, the method comprising administering a medicament comprising the sDR5-Fc recombinant fusion protein of claim 1 as an essential ingredient in the medicament, wherein the medicament is administered in a therapeutically effective amount to treat drug-induced liver injury.

8. The method of claim 7, wherein, the drug-induced liver injury is a liver injury induced by an antipyretic analgesic drug, a liver injury induced by an acetylcholinesterase inhibitor, or a liver injury induced by an anti-tuberculosis drug.

9. A method of treating autoimmune hepatitis in a subject, the method comprising administering a medicament comprising the sDR5-Fc recombinant fusion protein of claim 2 as an essential ingredient in the medicament, wherein the medicament is administered in a therapeutically effective amount to treat autoimmune hepatitis.

10. A method of treating drug-induced liver injury in a subject, the method comprising administering a medicament comprising the sDR5-Fc recombinant fusion protein of claim 2 as an essential ingredient in the medicament, wherein the medicament is administered in a therapeutically effective amount to treat drug-induced liver injury.

11. A method of treating autoimmune hepatitis in a subject, the method comprising administering a medicament comprising the nucleotide sequence of claim 5 as an essential ingredient in the medicament, wherein the medicament is administered in a therapeutically effective amount to treat autoimmune hepatitis.

12. A method of treating drug-induced liver injury in a subject, the method comprising administering a medicament comprising the nucleotide sequence of claim 5 as an essential ingredient in the medicament, wherein the medicament is administered in a therapeutically effective amount to treat drug-induced liver injury.

13. The method of claim 12, wherein, the drug-induced liver injury is a liver injury induced by an antipyretic analgesic drug, a liver injury induced by an acetylcholinesterase inhibitor, or a liver injury induced by an anti-tuberculosis drug.

14. The method of claim 13, wherein, the antipyretic analgesic drug is acetaminophen.

15. The method of claim 13, wherein, the acetylcholinesterase inhibitor is tacrine.

16. The method of claim 13, wherein, the anti-tuberculosis drug is isoniazid and/or rifampicin.

* * * * *